(12) United States Patent
Chan

(10) Patent No.: US 8,541,177 B2
(45) Date of Patent: Sep. 24, 2013

(54) TREATMENT AND DIAGNOSIS OF ABNORMAL BONE DENSITY WITH AN INHIBITOR OF THE GLYPICAN-SCLEROSTIN INTERACTION

(75) Inventor: Alan Barry Chan, Ruislip Middlesex (GB)

(73) Assignee: A Chan Holding B.V., Enschede (NL)

( * ) Notice: Subject to any disclaimer, the term of this patent is extended or adjusted under 35 U.S.C. 154(b) by 883 days.

(21) Appl. No.: 12/160,761

(22) PCT Filed: Jan. 15, 2007

(86) PCT No.: PCT/EP2007/000295
§ 371 (c)(1),
(2), (4) Date: Jul. 11, 2008

(87) PCT Pub. No.: WO2007/080129
PCT Pub. Date: Jul. 19, 2007

(65) Prior Publication Data
US 2010/0129378 A1    May 27, 2010

Related U.S. Application Data

(60) Provisional application No. 60/758,836, filed on Jan. 13, 2006.

(30) Foreign Application Priority Data

Jan. 13, 2006  (EP) .................................. 06000814

(51) Int. Cl.
*G01N 33/53* (2006.01)
*G01N 33/566* (2006.01)
*C12N 5/00* (2006.01)
*C07K 14/435* (2006.01)

(52) U.S. Cl.
USPC .............. 435/7.1; 435/7.2; 435/375; 530/350

(58) Field of Classification Search
None
See application file for complete search history.

(56) References Cited

FOREIGN PATENT DOCUMENTS

WO    WO 2008/092894 A1  *  8/2008

OTHER PUBLICATIONS

Warmington et al., J. Bone Miner. Res., 2004, vol. 19, pp. S56.*
Filmus, et al., Genome Biology, 2008, vol. 9:224.*
Cheng et al., Carcinogenesis, 2008, vol. 29(7):1319-1326.*
Riew et al., Calcif. Tissue Int., 1998, vol. 63:357-360.*
Warmington, et al. "Sclerostin Monoclonal Antibody Treatment of Osteoporotic Rats Completely Reverses One Year of Ovariectomy-Induced Systemic Bone Loss," *Journal of Bone and Mineral Research*, vol. 20, No. 9, Suppl. 1, p. S22, Sep. 2005.
Warmington, et al. "Sclerostin Antagonism in Adult Rodents, via Monoclonal Antibody Mediated Blockade, Increases Bone Mineral Density and Implicates Sclerostin as a Key Regulator of Bone Mass During Adulthood," *Journal of Bone and Mineral Research*, vol. 19, p. S56, Oct. 2004.
Ominsky, et al. "Sclerostin Monoclonal Antibody Treatment Increases Bone Strength in Aged Osteopenic Ovariectomized Rats," *Journal of Bone and Mineral Research*, vol. 21, Suppl. 1, p. S44, Sep. 2006.
van Bezooijen, et al. "Bone Morphogenetic Proteins and Their Antagonists: The Sclerostin Paradigm," *Journal of Endocrinological Investigation*, vol. 28, No. 8, Suppl., pp. 15-17, 2005.
van Bezooijen, et al. "Sclerostin Is an Osteocyte-Expressed Negative Regulator of Bone Formation, but Not a Classical BMP Antagonist," *The Journal of Experimental Medicine*, vol. 199, No. 6, pp. 805-814, Mar. 15, 2004.
Sutherland, et al. "Sclerostin Promotes the Apoptosis of Human Osteoblastic Cells: A Novel Regulation of Bone Formation," *Bone*, vol. 35, No. 4, pp. 828-835, Oct. 2004.
Kusu, et al. "Sclerostin Is a Novel Secreted Osteoclast-Derived Bone Morphogenetic Protein Antagonist with Unique Ligand Specificity," *The Journal of Biological Chemistry*, vol. 278, No. 26, pp. 24113-24117, Jun. 27, 2003.
van Bezooijen, et al. "*SOST*/Sclerostin, an Osteocyte-Derived Negative Regulator of Bone Formation," *Cytokine and Growth Factor Reviews*, vol. 16, No. 3, pp. 319-327, Jun. 2005.
Li, et al. "Sclerostin Binds to LRP5/6 and Antagonizes Canonical Wnt Signaling," *The Journal of Biological Chemistry*, vol. 280, No. 20, pp. 19883-19887, May 20, 2005.
Winkler, et al. "Sclerostin Inhibition of Wnt-3a-induced C3H10T1/2 Cell Differentiation Is Indirect and Mediated by Bone Morphogenetic Proteins," *The Journal of Biological Chemistry*, vol. 280, No. 4, pp. 2498-2502, Jan. 28, 2005.
Viviano, et al. "Altered Hematopoiesis in Glypican-3-Deficient Mice Results in Decreased Osteoclast Differentiation and a Delay in Endochondral Ossification," *Developmental Biology*, vol. 282, No. 1, pp. 152-162, Jun. 1, 2005.
Sheu, et al. "Use of a Phage Display Technique to Identify Potential Osteoblast Binding Sites Within Osteoclast Lacunae," *Journal of Bone and Mineral Research*, vol. 17, No. 5, pp. 915-922, May 5, 2002.
Paine-Saunders, et al. "*Glypican*-3 Controls Cellular Responses to Bmp4 in Limb Patterning and Skeletal Development," *Developmental Biology*, vol. 225, No. 1, pp. 179-187, Sep. 1, 2000.
Gutierrez, et al. "Changes in Secreted and Cell Associated Proteoglycan Synthesis During Conversion of Myoblasts to Osteoblasts in Response to Bone Morphogenetic Protein-2: Role of Decorin in Cell Response to BMP-2," *Journal of Cellular Physiology*, vol. 206, No. 1, pp. 58-67, Jan. 2006.
Capurro, et al. "Processing by Convertases is Not Required for Glypican-3-Induced Stimulation of Hepatocellular Carcinoma Growth," *The Journal of Biological Chemistry*, vol. 280, No. 50, pp. 41201-41206, Dec. 16, 2005.
International Search Report dated Apr. 27, 2007.
Balemans, et al. "Identification of the Disease-causing Gene in Sclerosteosis—Discovery of a Novel Bone Anabolic Target?" *J Musculoskel Neuron Interact*, vol. 4, No. 2, pp. 139-142, 2004.

* cited by examiner

*Primary Examiner* — Xiaozhen Xie
(74) *Attorney, Agent, or Firm* — Knobbe, Martens, Olson & Bear LLP

(57) ABSTRACT

Compositions and methods of treatment for abnormal bone density are disclosed based upon the finding that sclerostin must be bound to glypican in order to inhibit bone deposition. Methods for identifying agents that inhibit the glypican-sclerostin interaction are disclosed for treatment of bone deposition disorders. Diagnostic methods are also disclosed.

3 Claims, No Drawings

TREATMENT AND DIAGNOSIS OF ABNORMAL BONE DENSITY WITH AN INHIBITOR OF THE GLYPICAN-SCLEROSTIN INTERACTION

CROSS-REFERENCE TO RELATED APPLICATIONS

This application is the U.S. National Phase under 35 U.S.C. §371 of International Application PCT/EP2007/000295, filed Jan. 15, 2007, which claims priority to U.S. Provisional Application No. 60/758,836, filed Jan. 13, 2006 and EP 06000814.1, filed Jan. 13, 2006.

BACKGROUND TO THE INVENTION

Osteoporosis, or porous bone of low mass, is a disease characterized by inadequate bone density and structural deterioration of trabecular bone. This can lead to bone fragility and an increased susceptibility to fractures of the hip, spine and wrist. Osteoporosis, like high blood pressure, is a "silent disease" because bone loss occurs without symptoms and over a long period of time. People are frequently unaware they have osteoporosis until their bones become so weak that a sudden bump or fall causes a fracture or a vertebra to collapse. Osteoporosis is associated with high morbidity and poor quality of life.

The two primary bone cells are the osteoclasts and the osteoblasts. The osteoclasts are the cells that resorb, or breakdown, bone. They are of haemopoietic origin and develop from stem cells in the bone marrow. Mature functional osteoclasts are multinuclear cells and are localized on mineralized bone surfaces that these specialized cells can resorb. The osteoblasts, which are of mesenchymal origin, are the cells that build up bone. When the osteoblasts are finally encased in the mineralized matrix, the end stage phenotype, they are called osteocytes. The osteocytes are mechanosensory cells and respond to mechanical loading by generating signals for osteoclasts and osteoblasts lining the bone surface.

Bone is mainly built during foetal life, youth and adolescence. Once bones are formed, their shape and structure are continually renovated and modified by two processes known as modeling and remodelling. Both modeling and remodelling result in the replacement of old bone by new bone.

Modeling takes place during an individual's growth and is the main process through which the skeleton increases its volume and mass. In modeling, new bone is formed at a different location than where the bone was broken down. This results in a change in the shape of the skeleton and also is the cause for the increase in bone size. Depending on the lifestyle and dietary intake, bone mass can further increase until around the age of 30. This is called peak bone mass. Bone mass will stay more or less constant until around the age of 40 to 45. Thereafter, bone mass will decline gradually due to aging or rapidly, as in the case of post-menopausal osteoporosis.

The resorption of bone by osteoclasts and the subsequent formation by osteoblasts is called remodelling. This process takes place in an orderly fashion beginning with bone being eroded by osteoclasts, followed by refilling by osteoblasts at the resorption sites. In order to maintain bone mass constant bone resorption and bone formation are tightly coupled, a phenomenon called coupling. The molecular mechanisms responsible for this are still unclear. The remodelling process replaces old bone by new, ensures the correction of possible microdamages and enables the regulation of mineral homeostasis. During life, bone is remodelled constantly, but in healthy adults, a quantitative and qualitative balance is kept between bone formation and bone resorption to maintain bone mass constant. During aging or under certain pathological conditions, the balance between bone resorption and formation is disturbed leading to a gradual decrease in bone mass (as seen in old age osteoporosis) or to a rapid bone loss and destruction of bone architecture (as seen in post-menopausal osteoporosis).

In normal healthy individuals, the amount of bone formed during bone remodelling equals the amount of bone destroyed in order to maintain bone mass constant. When more bone is destroyed than formed bone loss occurs and bone diseases, such as osteoporosis, may develop. Osteoporosis is a crippling disease principally affecting the elderly and is characterized by low bone density leading to fractures and associated with high morbidity. The current FDA-approved drugs available only slow down bone loss or prevent further loss. Most drugs used to treat low bone mass are aimed at stopping the loss, not regaining bone density. This is due to the lack of understanding and knowledge of the molecular mechanisms of bone remodelling.

Conversely, when more bone is deposited than is destroyed, a phenotype of sclerosteosis may arise as seen, for example, in Simpson-Golabi-Behmel syndrome (SGBS), characterised by enlarged bones, most noticeably of the face. In SGBS, the patient typically presents with a broad, stocky appearance, large protruding jaw, widened nasal bridge and upturned nasal bridge. Infant mortality is high in SGBS patients, and early cardiac arrest is common in adults. No treatment for such sclerosteosis phenotype is available.

The present invention aims to provide compositions, method of treatment and methods of diagnosis of disorders related to abnormal bone density, which overcome the problems in the art.

SUMMARY OF THE INVENTION

The present invention provides the use of a composition comprising an inhibitor of the glypican-sclerostin interaction for the manufacture of a medicament for the treatment of a disorder relating to low bone mass, wherein said inhibitor is an antibody directed against glypican, sclerostin or a glypican-sclerostin complex.

The present invention further provides a method for identifying an inhibitor of the glypican-sclerostin interaction which method comprises measuring the displacement of glypican binding to sclerostin by a candidate inhibitor. Preferably said method comprises the steps of: a) contacting sclerostin with glypican in the presence and absence of the candidate inhibitor under conditions permitting the binding of the glypican to sclerostin; and b) measuring binding of the glypican to sclerostin wherein a decrease in binding in the presence of the candidate inhibitor, relative to binding in the absence of the candidate inhibitor, identifies the candidate inhibitor as an inhibitor of the glypican-sclerostin interaction.

The present invention also provides a method for identifying an inhibitor of the glypican-sclerostin interaction, said method comprising measuring the signalling response induced by the sclerostin-glypican interaction in the presence of said inhibitor, and comparing it with the signalling response induced by the sclerostin-glypican in the absence of said inhibitor. Preferably said method comprises the steps of: a) contacting sclerostin with glypican in the presence and absence of a candidate inhibitor; and b) measuring a signalling response induced by the sclerostin-glypican interaction, wherein a change in response in the presence of the candidate inhibitor of at least 10% compared with the response induced by glypican-sclerostin interaction in the absence of candidate inhibitor indicates the candidate inhibitor is identified as an inhibitor of the glypican-sclerostin interaction.

The present invention provides also a method for diagnosing a disorder or susceptibility to a disorder relating to low bone mass in a subject comprising the steps of: (a) measuring the glypican-sclerostin binding in said subject, and (b) comparing the binding in step (a) with the glypican-sclerostin binding of a healthy subject to determine the presence of a disorder relating to low bone mass.

The present invention provides the use of a composition comprising a glypican mimetic, which mimetic has the same, similar or improved functional effect as glypican binding to sclerostin, for the manufacture of a medicament for the treatment of a disorder relating to high bone mass, wherein said mimetic is an antibody or fragment thereof directed against sclerostin.

The present invention provides a method for identifying a glypican mimetic, which mimetic has the same, similar or improved functional effect as glypican binding to sclerostin, wherein the method comprises measuring the binding to sclerostin by a candidate mimetic. Preferably, said method comprises the steps of: a) contacting sclerostin with a candidate mimetic under conditions permitting the binding of the mimetic to sclerostin; and b) measuring binding of the mimetic to sclerostin, wherein the binding is at least 10% of the binding measured for the sclerostin-glypican interaction, indicates the candidate mimetic is identified as a glypican mimetic of the invention.

Additionally, the present invention provides a method for identifying a glypican mimetic, which mimetic has the same or similar functional effect as glypican binding to sclerostin, wherein the method comprises measuring the signalling response induced by the sclerostin-mimetic interaction, and comparing it with the signalling response induced by the sclerostin-glypican interaction. Preferably, said method comprises the steps of: a) contacting sclerostin with candidate mimetic; and b) measuring a signalling response induced by the sclerostin-mimetic interaction, wherein a signalling response that is at least 10% (e.g. equal to or more than 20%, 30%, 40%, 50%, 60%) of the signalling response measured for the sclerostin-glypican interaction indicates the candidate mimetic is identified as an glypican mimetic of the invention.

Also, the present invention provides a mimetic identified according to a method as described above.

Moreover, the present invention provides a method for diagnosing a disorder or susceptibility to a disorder relating to high bone mass in a subject comprising the steps of: (a) measuring the glypican-sclerostin binding in said subject, and (b) comparing the binding of step (a) with the glypican-sclerostin binding of a healthy subject to determine the presence of a disorder relating to high bone mass.

Further, the present invention provides a use of a composition comprising a glypican mimetic, which mimetic has the same, similar or improved functional effect as glypican binding to sclerostin, for the manufacture of a medicament for the treatment of a disorder relating to high bone mass The present invention provides additionally a method for diagnosing a disorder or susceptibility to a disorder relating to abnormal bone mass in a subject comprising the steps of: (a) obtaining the nucleotide sequence of glypican or sclerostin gene in said subject, and (b) comparing it to that of a healthy subject, where a mutation in the respective sclerostin or glypican gene indicates a disorder relating to abnormal bone mass or a susceptibility thereto, said mutation changing the binding and/or signalling of the glypican-sclerostin interaction compared with a healthy subject. Specifically, a decrease in binding and/or an increase in signalling indicates a disorder relating to high bone mass or susceptibility thereto, and an increase in binding and/or a decrease in signalling indicates a disorder relating to low bone mass or susceptibility thereto.

The present invention provides a vaccine and the use thereof, said vaccine comprising an immunogenic fragment of glypican or sclerostin for the treatment and/or prevention of disorder related to low bone mass.

DETAILED DESCRIPTION OF THE INVENTION

Unless defined otherwise, all technical and scientific terms used herein have the same meaning as is commonly understood by one of skill in the art. All publications referenced herein are incorporated by reference thereto. All United States patents and patent applications referenced herein are incorporated by reference herein in their entirety including the drawings.

The practice of the present invention will employ, unless otherwise indicated, conventional techniques of organic chemistry, pharmacology, molecular biology (including recombinant techniques), cell biology, biochemistry, and immunology, which are within the skill of the art. Such techniques are explained fully in the literature, such as, "Molecular Cloning: A Laboratory Manual "Second Edition (Sambrook et al., 1989); "Oligonucleotide Synthesis" (M. J. Gait, ed., 1984); "Animal Cell Culture" (R. I. Freshney, ed., 1987); the series "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calm, eds., 1987); "Current Protocols in Molecular Biology" (F. M. Ausubel et al., eds., 1987, and periodicals) "Polymerase Chain Reaction" (Mullis et al., eds., 1994); and "Current Protocols in Immunology" (J. E. Coligan et al., eds., 1991).

The articles "a" and "an" are used herein to refer to one or to more than one, i.e. to at least one of the grammatical object of the article. By way of example, "an inhibitor" means one inhibitor or more than one inhibitor.

As used herein, the term "comprising" is intended to mean that the compositions and methods include the recited elements, but not excluding others. "Consisting essentially of" 'when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of'" shall mean excluding more than trace elements of other ingredients and substantial method steps for administering the compositions of this invention. Embodiments defined by each of these transition terms are within the scope of this invention.

The recitation of numerical ranges by endpoints includes all integer numbers and, where appropriate, fractions subsumed within that range (e.g. 1 to 5 can include 1, 2, 3, 4 when referring to, for example, a number of inhibitors, and can also include 1.5, 2, 2.75 and 3.80, when referring to, for example, concentrations).

The present invention relates to the finding by the inventors that sclerostin inhibits bone deposition when bound to glypican, and in the absence of glypican, bone deposition resumes. Sclerostin is already known in the art as an integral protein controlling the deposit of new bone, since loss of the gene results in uncontrolled bone formation (e.g. sclerosteosis). Due to sclerostin's similarity in its cysteine-knot structure with the DAN family of TGF-β antagonists, sclerostin was originally hypothesised to be solely a bone morphogenic protein (BMP) antagonist (Brunkow et al. (2001) Am J Hum Genet, 68:577-589), however its ability to interact directly with BMPs has remained controversial.

The inventors have shown for the first time that an interaction exists between sclerostin and glypican, and such interaction is involved in BMP antagonism. Therapeutic modulation of this mechanism can result in increased or decreased bone density.

The inventors have also shown that Glypican-3 modulates the Wnt signalling pathway influencing bone mass through the Wnt pathway. Therefore, the interaction between sclerostin and glypican-3 is also antagonistic against the Wnt signalling pathway.

Thus, while the other factors have been implicated in the art in bone deposition via the Wnt and BMP signalling pathways, this is the first time these pathways have been disclosed to be modulated by the sclerostin and glypican interaction. It is also the first time a binding between sclerostin and glypican has been disclosed.

The present invention therefore relates to the finding by the inventors that in order for sclerostin to achieve its inhibitory effect, i.e. for sclerostin to inhibit bone deposition, it must be bound to glypican. It also relates to the finding that the sclerostin-glypican interaction modulates the Wnt and BMP pathways, which finding provides screening assays for modulators of bone deposition.

The finding by the inventors may be used in the treatment of disorders related to abnormal bone mass. For example, osteoporosis, characterised by low bone mass may be treated by inhibiting the glypican-sclerostin interaction. Alternatively, diseases characterised by high bone mass, may be treated by glypican, or a glypican mimetic which has the same or similar functional effect as glypican binding to sclerostin. The finding may also be used as a basis for identifying new agents for the treatment of abnormal bone mass. It may also be used to diagnose a disorder relating to abnormal bone mass or susceptibility thereto. It may also be used as a basis for a vaccine against low bone mass.

Inhibition of the Glypican-Sclerostin Interaction

One embodiment of the present invention is a method for the treatment of a disorder relating to low bone mass, which method comprises administering a composition comprising an inhibitor of the glypican-sclerostin interaction in an effective amount to a subject in need thereof. By "low bone mass" as used herein is meant an abnormally low bone mass for the size and weight of the subject.

Another embodiment of the present invention is a use of a composition comprising an inhibitor of the glypican-sclerostin interaction for the manufacture of a medicament for the treatment of a disorders relating to low bone mass.

Another embodiment of the present invention is a method for the treatment of a disorder relating to low bone mass, comprising the step of inhibiting glypican-sclerostin interaction in a subject in need thereof.

Another embodiment of the present invention is a method for identifying an agent for the treatment of low bone mass, which method comprises the step of identifying an agent that reduces the binding of glypican to sclerostin.

Another embodiment of the present invention is a method for identifying an agent for the treatment of low bone mass, which method comprises the use of an assay that measures the displacement of glypican binding to sclerostin by a candidate inhibitor.

Another embodiment of the present invention is a method for identifying an agent for the treatment of low bone mass, which method comprises the use of an assay that measures a change of sclerostin signalling caused by said agent compared with glypican.

Another embodiment of the present invention is a method for detecting the presence of an agent in a sample for the treatment of low bone mass, which method comprises the step of identifying an agent in the sample which reduces the binding of glypican to sclerostin.

Another embodiment is vaccine for the prevention and/or treatment of a disorder relating to low bone mass, comprising an immunogenic fragment of glypican and/or sclerostin.

Another embodiment is a use of an, immunogenic fragment of glypican and/or sclerostin for the manufacture of a vaccine for the prevention and/or treatment of a disorder relating to low bone mass.

Disorders relating to low bone mass include disorders such as osteoporosis, tumour or malignancy-induced bone loss, oral bone loss, tooth loss, and arthritis-induced bone loss.

—Inhibitor of the Glypican-Sclerostin Interaction

An inhibitor according to the invention is a molecule directed against sclerostin and/or glypican. The inhibitor has the effect of reducing or completely blocking the binding of glypican to sclerostin. The inhibitor may decrease the binding of sclerostin to glypican by at least 10%, 20%, 30%, 40%, 50%, 60%, 70%, 80%, 90% in the presence of inhibitor, as compared to the binding in the absence of inhibitor, or by an amount in the range between any two of the aforementioned values. Preferably, the inhibitor decreases said binding by at least 10%. The binding can be determined by, for example, measuring the binding constant using biochemical and/or biophysical methods as described herein.

An inhibitor of the invention may also change the signalling response induced by the sclerostin-glypican interaction by at least 10%, 20%, 30%, 40%, 50%, 60%, 70%, 80%, 90% in the presence of inhibitor, as compared to the signalling in the absence of inhibitor, or by an amount in the range between any two of the aforementioned values. Preferably, the inhibitor changes said signalling by at least 10%. The signalling can be determined by methods well known in the art, such as for example, by measuring signalling levels using a reporter construct as described below.

An inhibitor, useful according to the present invention, includes, but is not limited to a polypeptide, a peptide, an antibody or antigen-binding fragment thereof which is directed against at least a portion of glypican, sclerostin or the glypican-sclerostin complex. An inhibitor can be an antibody-like molecule comprising one or more non-immunoglobulin constant domains and a variable domain e.g. Affibodies™ (Andersson, M., at al. (2003) *J. Immunol. Meth.* 283(1-2):225-34). Libraries of such non-immunoglobulin molecules can be readily screened for the suitable inhibitors. An inhibitor may further include a lipid, a carbohydrate, a nucleic acid, and a small organic molecule. Candidate inhibitors can be natural or synthetic compounds, including, for example, synthetic small molecules, compounds contained in extracts of animal, plant, bacterial or fungal cells, as well as conditioned medium from such cells. Inhibitory compounds can be determined using the methods described below.

—Antibodies

As used herein, an antibody according to the present invention is the conventional immunoglobulin molecule, as well as fragments thereof which are also specifically reactive with glypican and/or sclerostin. Antibodies can be fragmented using conventional techniques and the fragments screened for utility in the same manner as described herein below for whole antibodies. For example, $F(ab)_2$ fragments can be generated by treating antibody with pepsin. The resulting $F(ab)_2$ fragment can be treated to reduce disulfide bridges to produce Fab fragments. The antibody of the present invention is further intended to include bispecific, single-chain (scFv), VHH (Camelidae) and chimeric and humanised molecules having affinity for glypican and/or sclerostin conferred by at least one CDR region of the antibody. The antibody may further comprise a label attached thereto and able to be detected, (e.g., the label can be a radioisotope, fluorescent compound, chemiluminescent compound, enzyme, or enzyme co-factor).

Inhibitors (and agents) according to the invention include but are not limited to monoclonal or polyclonal antibodies or hypervariable portions of the antibodies. The term "humanised immunoglobulin" as used herein refers to an immunoglobulin comprising portions of immunoglobulins of a different origin, wherein at least one portion is of human origin. Accordingly, the present invention also relates to a humanised immunoglobulin which binds glypican, sclerostin or to the complex, said immunoglobulin comprising an antigen-binding region of nonhuman origin (e.g., rodent) and at least a portion of an immunoglobulin of human origin (e.g., a human framework region, a human constant region or portion thereof). Nucleic acid (e.g., DNA) sequences coding for humanised variable regions can be constructed using PCR mutagenesis methods to alter DNA sequences encoding a human or humanized chain, such as a DNA template form a previously humanized variable region (see e.g., Kamman, M., et al., Nucleic Acids Res., 17: 5404 (1989); Sato, K., et al., Cancer Research, 53: 851-856 (1993); Daugherty, B. L. et al., Nucleic Acids Res., 19(9): 2471-2476 (1991); and Lewis, A. P. and J. S Crowe, Gene, 101: 297-302 (1991)). Using these or other suitable methods, variants can also be readily produced. In one embodiment, cloned variable regions can be mutagenised, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993; Knappik et al., WO 97/08320, published Mar. 6, 1997).

An antibody according to the invention is directed against sclerostin, glypican or the sclerostin-glypican complex. In binding it disrupts the functional sclerostin-glypican complex. Preferably, it binds in the vicinity of the respective glypican or sclerostin binding site so as to act to sterically hinder normal binding.

Inhibitors of the glypican-sclerostin interaction may be identified by displacements assays and by monitoring the signalling of sclerostin in biochemical assays as described below.

—Binding and Displacement Assays

Inhibitors of the glypican-sclerostin interaction can be identified by displacement assays which measure a reduction of the interaction by a candidate inhibitor i.e. the displacement of the normal binding partner.

According to an embodiment of the invention, an inhibitor of the glypican-sclerostin interaction may be identified by a method comprising the steps of: a) contacting sclerostin with glypican in the presence and absence of the candidate inhibitor under conditions permitting the binding of the glypican to sclerostin; and b) measuring binding of the glypican to sclerostin wherein a decrease in binding in the presence of the candidate inhibitor, relative to binding in the absence of the candidate inhibitor, identifies the candidate inhibitor as an inhibitor of the glypican-sclerostin interaction.

The measuring may be performed using a method selected from label displacement, surface plasmon resonance, fluorescence resonance energy transfer (FRET) or bioluminescence resonance energy transfer (BRET), fluorescence quenching, and fluorescence polarization. Such techniques are described in detail below.

As used herein, the term "binding" refers to the physical association of a component (e.g., sclerostin) with another component (e.g., glypican). A measurement of binding can lead to a value such as a dissociation constant, an association constant, on-rate or off-rate.

As used herein, the term "conditions permitting the binding." refers to conditions of, for example, temperature, salt concentration, pH and protein concentration under which binding will arise. Exact binding conditions will vary depending upon the nature of the assay, for example, whether the assay uses pure proteins or only partially purified proteins. Temperatures for binding can vary from 15 deg C. to 37 deg C., but will preferably be between room temperature and about 30 deg C. The concentration of sclerostin in a binding reaction will also vary, but will preferably be about 10 pM to 10 nM (e.g., in a reaction using radiolabeled components).

For displacement experiments, cells expressing sclerostin or sclerostin as such may be incubated in binding buffer with labelled glypican in the presence or absence of increasing concentrations of a candidate inhibitor. To validate and calibrate the assay, control competition reactions using increasing concentrations of unlabeled glypican can be performed. After incubation, a washing step is performed to remove unbound glypican. Bound, labelled glypican is measured as appropriate for the given label (e.g., scintillation counting, fluorescence, antibody-dye etc.). A decrease of at least 10% (e.g., at least 20%, 30%, 40%, 50%, or 60%) in the amount of labelled glypican bound in the presence of candidate inhibitor indicates displacement of binding by the candidate inhibitor. Candidate inhibitor may be considered to bind specifically in this or other assays described herein if they displace at least 10%, 20%, 30%, 40%, 50%, 60% and preferably at least 10% of labelled glypican (sub-saturating glypican dose) at a concentration of 1 mM or less. Of course, the roles of glypican and sclerostin may be switched; the skilled person may adapt the method so sclerostin is applied to glypican in the presence of various concentrations of candidate inhibitor to determine displacement.

As the term is used herein, binding is "specific" if it occurs with a Kd of 1 mM or less, generally in the range of 100 nM to 10 pM. For example, binding is specific if the Kd is 100 nM, 50 nM, 10 nM, 1 nM, 950 pM, 900 pM, 850 pM, 800 pM, 750 pM, 700 pM, 650 pM, 600 pM, 550 pM, 500 pM, 450 pM, 350 pM, 300 pM, 250 pM, 200 pM, 150 pM, 100 pM, 75 pM, 50 pM, 25 pM, 10 pM or less.

Displacement of binding can be monitored by surface plasmon resonance (SPR). Surface plasmon resonance assays can be used as a quantitative method to measure binding between two molecules by the change in mass near an immobilised sensor caused by the binding or loss of binding of glypican from the aqueous phase to sclerostin immobilized on the sensor. This change in mass is measured as resonance units versus time after injection or removal of the glypican or candidate inhibitor and is measured using a Biacore Biosensor (Biacore AB). Sclerostin can be immobilised on a sensor chip (for example, research grade CM5 chip; Biacore AB) according to methods described by Salamon et al. (Salamon et al., 1996, Biophys. J. 71: 283-294; Salamon et al., 2001, Biophys. J. 80: 1557-1567; Salamon et al., 1999, Trends Biochem. Sci. 24: 213-219, each of which is incorporated herein by reference.). Sarrio et al. demonstrated that SPR can be used to detect ligand binding to the GPCR A(1) adenosine receptor immobilized in a lipid layer on the chip (Sarrio et al., 2000, Mol. Cell. Biol. 20: 5164-5174, incorporated herein by reference). Conditions for glypican binding to sclerostin in an SPR assay can be fine-tuned by one of skill in the art using the conditions reported by Sarrio et al. as a starting point.

SPR can assay for inhibitors of binding in at least two ways. First, glypican can be pre-bound to immobilised sclerostin, followed by injection of candidate inhibitor at a concentration ranging from 0.1 nM to 1 µM. Displacement of the bound glypican can be quantitated, permitting detection of inhibitor binding. Alternatively, the chip-bound sclerostin can be pre-incubated with candidate inhibitor and challenged with glypican. A difference in glypican binding to sclerostin exposed to inhibitor relative to that on a chip not pre-exposed to inhibitor will demonstrate binding or displacement of glypican in the presence of inhibitor. In either assay, a decrease of 10% (e.g., 20%, 30%, 40%, 50%, 60%) or more in the amount of glypican bound in the presence of candidate inhibitor, relative to the amount of a glypican bound in the absence of candidate inhibitor that the candidate inhibitor inhibits the interaction of sclerostin and glypican. While sclerostin is immobilised in the above, the skilled person may readily adapt the method so that glypican is the immobilised component.

Another method of detecting inhibition of binding of glypican to sclerostin uses fluorescence resonance energy transfer (FRET). FRET is a quantum mechanical phenomenon that occurs between a fluorescence donor (D) and a fluorescence acceptor (A) in close proximity to each other (usually <100 angstroms of separation) if the emission spectrum of D overlaps with the excitation spectrum of A. The molecules to be tested, e.g., glypican and sclerostin, are labelled with a complementary pair of donor and acceptor fluorophores. While bound closely together by the sclerostin:glypican interaction, the fluorescence emitted upon excitation of the donor fluorophore will have a different wavelength than that emitted in response to that excitation wavelength when the glypican and sclerostin are not bound, providing for quantitation of bound versus unbound molecules by measurement of emission intensity at each wavelength. Donor fluorophores with which to label the sclerostin are well known in the art. Of particular interest are variants of the *A. victoria* GFP known as Cyan FP (CFP, Donor (D)) and Yellow FP (YFP, Acceptor (A)). As an example, the YFP variant can be made as a fusion protein with sclerostin. Vectors for the expression of GFP variants as fusions (Clontech) as well as fluorophore-labelled glypican compounds (Molecular Probes) are known in the art. The addition of a candidate inhibitor to the mixture of labelled glypican and YFP-sclerostin will result in an inhibition of energy transfer evidenced by, for example, a decrease in YFP fluorescence relative to a sample without the candidate inhibitor. In an assay using FRET for the detection of sclerostin:glypican interaction, a 10% or greater (e.g. equal to or more than 20%, 30%240%, 50%, 60%) decrease in the intensity of fluorescent emission at the acceptor wavelength in samples containing a candidate inhibitor, relative to samples without the candidate inhibitor, indicates that the candidate inhibitor inhibits the sclerostin:glypican interaction.

A variation on FRET uses fluorescence quenching to monitor molecular interactions. One molecule in the interacting pair can be labelled with a fluorophore, and the other with a molecule that quenches the fluorescence of the fluorophore when brought into close apposition with it. A change in fluorescence upon excitation is indicative of a change in the association of the molecules tagged with the fluorophore:quencher pair. Generally, an increase in fluorescence of the labelled sclerostin is indicative that the glypican molecule bearing the quencher has been displaced. Of course, a similar effect would arise when glypican is fluorescently labelled and sclerostin bears the quencher. For quenching assays, a 10% or greater increase (e.g., equal to or more than 20%, 30%, 40%, 50%, 60%) in the intensity of fluorescent emission in samples containing a candidate inhibitor, relative to samples without the candidate inhibitor, indicates that the candidate inhibitor inhibits sclerostin:glypican interaction.

In addition to the surface plasmon resonance and FRET methods, fluorescence polarization measurement is useful to quantitate binding. The fluorescence polarization value for a fluorescently-tagged molecule depends on the rotational correlation time or tumbling rate. Complexes, such as those formed by sclerostin associating with a fluorescently labelled glypican, have higher polarization values than uncomplexed, labelled glypican. The inclusion of a candidate inhibitor of the sclerostin:glypican interaction results in a decrease in fluorescence polarization, relative to a mixture without the candidate inhibitor, if the candidate inhibitor disrupts or inhibits the interaction of sclerostin with glypican. Fluorescence polarization is well suited for the identification of small molecules that disrupt the formation of complexes. A decrease of 10% or more (e.g., equal to or more than 20%, 30%, 40%, 50%, 60%) in fluorescence polarization in samples containing a candidate inhibitor, relative to fluorescence polarization in a sample lacking the candidate inhibitor, indicates that the candidate inhibitor inhibits sclerostin:glypican interaction.

Another detection system is bioluminescence resonance energy transfer (BRET), which uses light transfer between fusion proteins containing a bioluminescent luciferase and a fluorescent acceptor. In general, one molecule of the sclerostin:glypican interacting pair is fused to a luciferase (e.g. *Renilla luciferase* (Rluc))—a donor which emits light in the wavelength of ~395 nm in the presence of luciferase substrate (e.g. DeepBlueC). The other molecule of the pair is fused to an acceptor fluorescent protein that can absorb light from the donor, and emit light at a different wavelength. An example of a fluorescent protein is GFP (green fluorescent protein) which emits light at ~510 nm. The addition of a candidate inhibitor to the mixture of donor fused-glypican and acceptor-fused-sclerostin will result in an inhibition of energy transfer evidenced by, for example, a decrease in acceptor fluorescence relative to a sample without the candidate inhibitor. In an assay using BRET for the detection of sclerostin:glypican interaction, a 10% or greater (e.g. equal to or more than 20%, 30%, 40%, 50%, 60%) decrease in the intensity of fluorescent emission at the acceptor wavelength in samples containing a candidate inhibitor, relative to samples without the candidate inhibitor, indicates that the candidate inhibitor inhibits the sclerostin:glypican interaction.

It should be understood that any of the binding assays described herein can be performed with a non-glypican ligand (for example, agonist, antagonist, etc.) of sclerostin, e.g., a small molecule identified as described herein or glypican mimetics including but not limited to any of natural or synthetic peptide, a polypeptide, an antibody or antigen-binding fragment thereof, a lipid, a carbohydrate, and a small organic molecule.

Any of the binding assays described can be used to determine the presence of an inhibitor in a sample, e.g., a tissue sample, that binds to the sclerostin, or that affects the binding of glypican to sclerostin. To do so, sclerostin is reacted with glypican in the presence or absence of the sample, and binding is measured as appropriate for the binding assay being used. A decrease of 10% or more (e.g., equal to or more than 20%, 30%, 40%, 50%, 60%) in the binding of glypican indicates that the sample contains an inhibitor that modulates glypican binding to the sclerostin.

Any of the binding assays described can also be used to determine the presence of an inhibitor in a library of compounds. Such screening techniques using, for example, high throughput screening are well known in the art.

—Signalling Assays

Inhibitors of the glypican-sclerostin interaction can be identified by signalling assays.

According to another embodiment of the invention, an inhibitor of the glypican-sclerostin interaction may be identified by a method comprising the steps: a) contacting sclerostin with glypican in the presence and absence of a candidate inhibitor; and b) measuring a signalling response induced by the sclerostin-glypican interaction, wherein a change in response in the presence of the candidate inhibitor of at least 10% (e.g., at least 20%, 30%, 40%, 50%, 60%, 70%, 80%, 90%) compared with the response induced by glypican-sclerostin interaction in the absence of candidate inhibitor indicates the candidate inhibitor is identified as an inhibitor of the glypican-sclerostin interaction. The change can be an increase or a decrease depending on the monitored activity.

The signalling response is preferably the response of the Wnt and/or the BMP pathway, in which case an inhibitor would cause an increase in Wnt and/or BMP pathway activities. The signalling response can be determined, for example, measuring signalling levels using a reporter construct. For example, a suitable mammalian cell displaying glypican or sclerostin may be transfected with a reporter construct comprising a promoter which is responsive to Wnt and/or BMP. When sclerostin binds glypican, inhibiting the Wnt and/or BMP pathways, expression of a report protein is inhibited, which reduction can be measured, for example, by immunoassay, fluorescence, light measurement, etc., depending on the nature of the reporter protein. The expression is measured in the presence and absence of candidate inhibitor.

By way of a specific example, a reporter construct may be a modified Wnt-responsive luciferase reporter construct (TBE-luc) comprising a minimal Wnt responsive promoter (4 repeats of TCF-4 binding element) driving expression of an E1-Gal4VP16 fusion product combined with a responsive UAS-luciferase reporter. This together with a Wnt expression vector (such as expression constructs for mouse Wnt1, human/mouse hybrid Wnt3, and mouse Wnt3a) may be transfected into KS483 osteoprogenitor cells, C3H10T1/2, or U2OS, or any other suitable cell line. The transfected cell leads to activation of the UAS-luciferase reporter, which activation can be blocked by sclerostin.

—Diagnosing Low Bone Mass

Another embodiment of the present invention is a method for diagnosing a disorder or susceptibility to a disorder relating to low bone mass in a subject comprising the step of measuring the glypican-sclerostin binding in said subject and comparing the binding with that of a healthy subject to determine the presence of a disorder relating to low bone mass or susceptibility thereof. Compared with a healthy subject, the binding may be at least 10%, 20%, 30%, 40%, 50%, 60%, 70%, 80%, and preferably at least 20% higher than the binding observed in a healthy subject.

The measuring may be performed using a method selected from biochemical assay (e.g., solid phase assay), surface plasmon resonance, fluorescence resonance energy transfer, bioluminescence resonance energy transfer (BRET), fluorescence quenching, and fluorescence polarisation. Such techniques are described above in detail for identifying inhibitory compounds. However, such methods can be readily adapted to measuring binding between glypican and sclerostin.

Biochemical assays generally rely on the immobilisation of one binding component for example of a membrane or other solid support, and exposure to a ligand. After washing away excess ligand, bound ligand is detected by immunoassay, or by using labelled ligand (e.g., radio-labelled ligand, fluorescently labelled ligand, particulate labelled ligand etc.). For example, sclerostin may be immobilised onto magnetic beads and exposed to glypican at various concentrations. Bound glypican can be detected using primary and secondary antibody immunoassays to arrive at a binding constant. Alternatively, the skilled person may adapt the method so glypican is immobilised and sclerostin is applied to determine binding.

Surface plasmon resonance assays can be used as a quantitative method to measure binding between two molecules as already described above. Chip-bound sclerostin can be contacted with glypican to arrive at a binding constant. Binding reactions can be performed at different glypican concentrations if necessary to arrive at a binding constant. While sclerostin is immobilised in the above, the skilled person may readily adapt the method with glypican being the immobilised component.

FRET may also be used to determine binding between glypican and sclerostin. The glypican and sclerostin, are labelled with a complementary pair of donor and acceptor fluorophores. While bound closely together by the sclerostin: glypican interaction, the fluorescence emitted upon excitation of the donor fluorophore will have a different wavelength than that emitted in response to that excitation wavelength when the glypican and sclerostin are not bound, providing for quantitation of bound versus unbound molecules by measurement of emission intensity at each wavelength. Binding reactions can be performed at different glypican concentrations to arrive at a binding constant.

BRET, described above, may also be used to determine glypican: sclerostin binding. Light is emitted by the acceptor when in close proximity to the donor, i.e., when a glypican-sclerostin complex is formed. By measuring the interaction under a range of concentration and conditions, a binding constant for the interaction can be determined.

Fluorescence quenching fluorescence as described above similarly provides an indication of bound versus unbound molecules. Generally, an decrease in fluorescence of the labelled sclerostin is indicative that the glypican molecule bearing the quencher has bound. Of course, a similar effect would arise when glypican is fluorescently labelled and sclerostin bears the quencher. Binding reactions can be performed at different glypican concentrations to arrive at a binding constant.

Fluorescence polarisation measurement as described above can also determine binding between sclerostin and glypican. Complexes, such as those formed by sclerostin associating with a fluorescently labelled glypican, would have higher polarisation values than uncomplexed, labelled sclerostin. Binding reactions can be performed at different mimetic concentrations to arrive at a binding constant.

—Vaccination for the Treatment of Low Bone Mass

The finding that the sclerostin-glypican interaction influences bone deposition is the basis for a vaccine for the treatment of low bone mass. A vaccine comprises immunogenic fragments of glypican, sclerostin or both. The vaccine results in the production of anti-glypican and/or anti-sclerostin antibodies by the immune system of a subject after administration. The antibodies bind glypican and/or sclerostin, inhibiting the glypican-sclerostin interaction. The result is reduced inhibition of the Wnt pathway, and a concomitant increase in bone deposition.

An immunogenic fragment may be a portion of a polypeptide which comprises an immunogenic patch, against which antibodies can be raised after administration to the subject. An immunogenic fragment gives rise to antibodies which bind to sclerostin or glypican, or both, inhibiting the sclerostin-glypican interaction. The immunogenic fragment may be derived from the glypican binding site or sclerostin, or from the sclerostin binding site of glypican. The vaccine may comprise, in addition to immunogenic fragments, one or more adjuvants, such as incomplete Freund's adjuvant, aluminium phosphate, aluminium hydroxide, or alum, which materials are well known in the art.

Modulation of Sclerostin by Glypican or Glypican Mimetic

The present invention also provides a method for the treatment of a disorder relating to high bone mass, which method comprises administering a composition comprising a glypican mimetic that modulates a function of sclerostin, which function is normally modulated by glypican in an effective amount to a subject in need thereof. By "high bone mass" as used herein is meant an abnormally high bone mass for the size and weight of the subject.

The present invention also provides a use of a composition comprising a glypican mimetic for the manufacture of a medicament for the treatment of a disorder relating to high bone mass.

The present invention also provides a method for the treatment of a disorder relating to high bone mass, comprising the step of modulating a function of sclerostin, which function is normally modulated by glypican in a subject in need thereof.

The present invention also provides a method for identifying a glypican mimetic for the treatment of high bone mass, which method comprises the step of identifying a compound that modulates a function of sclerostin, which function is normally modulated by glypican.

The present invention also provides a method for identifying a glypican mimetic for the treatment of high bone mass, which method comprises the use of an assay that measures the binding to sclerostin by a candidate glypican mimetic.

The present invention also provides a method for identifying a glypican mimetic for the treatment of high bone mass, which method comprising the use of an assay that measures a change of sclerostin signalling caused by said mimetic compared with glypican.

The present invention also provides a method for detecting the presence of a glypican mimetic in a sample for the treatment of high bone mass, which method comprises the step of identifying a compound in a sample which modulates a function of sclerostin, which function is normally modulated by glypican.

Disorders relating to high bone mass include type II sclerosteosis. Type II sclerosteosis is characterised by bone overgrowth, and phenotypically similar to the classical scleroteosis (Type I). Type II sclerosteosis is caused by a mutation or SNP in the glypican gene which mutation prevents binding to sclerostin. Examples of Type II scleroteosis include Simpson Golabi Behmel syndrome, Bulldog syndrome, Dysplasia gigantism syndrome, X-linked, Golabi-Rosen syndrome, and Simpson dysmorphia syndrome. Typically, these diseases indicate bone overgrowth especially in the skull.

—Glypican Mimetics

A glypican mimetic or mimetic is a compound that has the same, similar or improved functional effect as glypican binding to sclerostin. It may be a compound that contains an arrangement of functional groups often with additional hydrophobic or charged groups to resemble the active confirmation of the binding region of the native glypican structure. It is to be understood that a glypican mimetic may also include native glypican. By imitating the effect of the glypican, the inhibitory effect of sclerostin is maintained or increased in the body, so bone deposition is inhibited.

According to one aspect of the invention, a mimetic exhibits at least 10%, 20%, 30%, 40%, 50%, 60%, 70%, 80%, 90% of the binding of glypican for sclerostin or a value in the range between any two of the aforementioned values. Preferably, the mimetic exhibits at least 20% of the binding activity of glypican for sclerostin.

According to one aspect of the invention, a mimetic exhibits at least 10%, 20%, 30%, 40%, 50%, 60%, 70%, 80%, 90% of the signalling activity of glypican or a value in the range between any two of the aforementioned values. Preferably, the mimetic exhibits at least 20% of the signalling activity of glypican.

A mimetic, useful according to the present invention, includes, but is not limited to a polypeptide, a peptide, an antibody or antigen-binding fragment thereof which specifically binds to at least a portion of the glypican binding site of sclerostin, a lipid, a carbohydrate, a nucleic acid, and a small organic molecule. Candidate mimetics can be natural or synthetic compounds, including, for example, synthetic small molecules, compounds contained in extracts of animal, plant, bacterial or fungal cells, as well as conditioned medium from such cells. Mimetic compounds can be determined using the methods described below.

—Binding Assays for Detecting Glypican Mimetics

According to one embodiment of the invention, a glypican mimetic is identified by a method comprising the steps: a) contacting sclerostin with candidate mimetic under conditions permitting the binding of the mimetic to sclerostin; and b) measuring binding of the mimetic to sclerostin, wherein the binding is at least 10% (e.g., at least 20%, 30%, 40%, 50%, 60%, 70%, 80% or 90%) of the binding measured for the sclerostin-glypican interaction, indicates the candidate mimetic is identified as a glypican mimetic of the invention.

The measuring may be performed using a method selected from biochemical assay (e.g., solid phase assay), surface plasmon resonance, fluorescence resonance energy transfer, fluorescence quenching, and fluorescence polarisation. Such techniques have been described above in detail for diagnosing disorders.

Biochemical assays generally rely on the immobilisation of one binding component, for example, of a membrane or other solid support, and exposure to a ligand. After washing away excess ligand, bound ligand is detected by immunoassay, or by using labelled ligand (e.g., radio-labelled ligand, fluorescently labelled ligand, particulate labelled ligand etc.). For example, sclerostin may be immobilised onto magnetic beads and exposed to a mimetic at various concentrations. Bound mimetics can be detected using primary and secondary antibody, immunoassays to arrive at a binding constant. Of course, the roles of a mimetic and sclerostin may be switched; the skilled person may adapt the method so sclerostin is applied to a mimetic to determine binding.

Surface plasmon resonance assays can be used as a quantitative method to measure binding between two molecules as already described above. Chip-bound sclerostin can be challenged with a candidate mimetic to determine binding. Binding reactions can be performed at different mimetic concentrations if necessary to arrive at a binding constant. A mimetic:sclerostin binding which is at least 10% (e.g., at least 20%, 30%, 40%, 50%, 60%, 70%, 80% or 90%) of the binding of glypican:sclerostin is considered a glypican mimetic. While sclerostin is immobilised in the above, the skilled person may readily adapt the method so that the mimetic is the immobilised component.

FRET may also be used to determine binding between the mimetic and sclerostin. The mimetic and sclerostin are labelled with a complementary pair of donor and acceptor fluorophores. While bound closely together by the sclerostin: mimetic interaction, the fluorescence emitted upon excitation of the donor fluorophore will have a different wavelength than that emitted in response to that excitation wavelength when the mimetic and sclerostin are not bound, providing for quantitation of bound versus unbound molecules by measurement of emission intensity at each wavelength. Binding reactions can be performed at different mimetic concentrations if necessary to arrive at a binding constant.

BRET may also be used to determine mimetic:sclerostin binding. As already mentioned above, light is emitted by the acceptor when in close proximity to the donor, i.e., when a mimetic-sclerostin complex is formed. By measuring the interaction under a range of concentrations and conditions, a binding constant for the interaction can be determined.

Fluorescence quenching fluorescence as described above similarly provides an indication of bound versus unbound molecules. Generally, a decrease in fluorescence of the labelled sclerostin is indicative that the mimetic molecule bearing the quencher has bound. Of course, a similar effect would arise when a mimetic is fluorescently labelled and sclerostin bears the quencher. Binding reactions can be performed at different mimetic concentrations if necessary to arrive at a binding constant. For quenching assays, a 10% or greater (e.g., equal to or more than 20%, 30%, 40%, 50%, 60%) decrease in the intensity of fluorescent emission, indicates that the candidate mimetic binds sclerostin. Control experiments using quench-labelled sclerostin and glypican can establish expected levels of quenching; a quenching observed with a mimetic would be at least 10% (e.g., at least 20%, 30%, 40%, 50%, 60%, 70%, 80% or 90%) of the level observed with glypican.

Fluorescence polarisation measurement as described above can also determine binding between sclerostin and a mimetic. Complexes, such as those formed by sclerostin associating with a fluorescently labelled mimetic, would have higher polarisation values than uncomplexed, labelled sclerostin. An increase of 10% or more (e.g., equal to or more than 20%, 30%, 40%, 50%, 60%) in fluorescence polarisation in samples containing a candidate mimetic, relative to fluorescence polarization in a sample lacking the candidate mimetic, indicates the presence of a mimetic. Binding reactions can be performed at different mimetic concentrations if necessary to arrive at a binding constant. Control experiments using sclerostin and glypican can establish expected levels of polarization.

Any of the binding assays described can be used to determine the presence of a mimetic in a sample, e.g., a tissue sample that binds to sclerostin. To do so, sclerostin is reacted in the presence or absence of the sample, and binding is measured as appropriate for the binding assay being used. An increase of 10% or more (e.g., equal to or more than 20%, 30%, 40%, 50%, 60%) in the binding of sclerostin indicates that the sample contains a mimetic that binds to sclerostin.

Any of the binding assays described can also be used to determine the presence of a mimetic in a library of compounds. Such screening techniques using, for example, high throughput screening are well known in the art.

—Signalling Assays for Detecting Glypican Mimetics

According to one embodiment of the invention, a mimetic may be identified by a method comprising the steps of: a) contacting sclerostin with a candidate mimetic; and b) measuring a signalling response induced by the sclerostin-mimetic interaction, wherein a signalling response that is at least 10% (e.g., equal to or more than 20%, 30%, 40%, 50%, 60%) of the signalling response measured for the sclerostin-glypican interaction indicates the candidate mimetic is identified as an glypican mimetic of the invention.

The signalling response is preferably the response of the Wnt and/or BMP pathway, in which case a mimetic would cause a decrease in Wnt and/or BMP pathway activities compared with the non-stimulated state. The signalling response can be determined, for example, by measuring signalling levels using a reporter construct as already mentioned above. When sclerostin binds a mimetic, inhibiting the Wnt and/or BMP pathway, expression of a reporter protein is inhibited, which reduction can be measured, for example, by immunoassay, fluorescence, light measurement, etc., depending on the nature of the reporter protein. The expression can also be measured for the sclerostin-glypican interaction.

The example using the Wnt-responsive luciferase reporter construct described above can be readily adapted to the detection of glypican mimetics by the measurement of signaling.

Any of the binding assays described can be used to determine the presence of a mimetic in a sample, e.g., a tissue sample that binds to the sclerostin. To do so, sclerostin is reacted in the presence or absence of the sample, and signalling is measured as appropriate for the assay being used. An increase of 10% or more (e.g., equal to or more than 20%, 30%, 40%, 50%, 60%) in the signalling of sclerostin indicates that the sample contains a mimetic that binds to sclerostin.

Any of the signalling assays described can also be used to determine the presence of a mimetic in a library of compounds. Such screening techniques using, for example, high throughput screening are well known in the art.

—Diagnosing Disorders Relating to High Bone Mass

The present invention also provides a method for diagnosing a disorder or susceptibility to a disorder relating to high bone mass in a subject. Preferably said method comprises the step of measuring the glypican-sclerostin binding in a subject and comparing the binding constant with that of a healthy subject to determine the presence of a disorder relating to high bone mass or susceptibility thereof. Compared with a healthy subject, the binding may be at least 10%, 20%, 30%, 40%, 50%, 60%, 70%, 80%, and preferably at least 10% less than the binding observed in a healthy subject.

Binding assays suitable for measuring the glypican-sclerostin are described in detail above.

Sequence Analysis for Diagnosing Abnormal Bone Mass

Mutations in the sclerostin or glypican gene in a subject may be predictors of developing a disorder relating to abnormal bone mass, and/or can be used to make a diagnosis. Such mutations change the interactions between the sclerostin and glypican, i.e., cause an increase or decrease the binding and signalling compared with a healthy subject.

One embodiment of the present invention is a method for diagnosing a disorder or susceptibility to a disorder relating to abnormal bone mass in a subject comprising the step of obtaining the DNA nucleotide sequence of glypican or sclerostin gene in said subject and comparing it to that of a healthy subject, where a mutation in the respective sclerostin or glypican gene indicates a disorder relating to abnormal bone mass or a susceptibility thereto.

Another embodiment of the present invention is a method for diagnosing a disorder or susceptibility to a disorder relating to abnormal bone mass in a subject comprising the step of obtaining the DNA nucleotide sequence of glypican or sclerostin in said subject and comparing it to that of a healthy subject, where a presence of a mutation that changes binding respectively to sclerostin or glypican compared with a healthy subject indicates a disorder relating to abnormal bone mass or a susceptibility thereto.

Mutations may be present in the non-translated portions of a gene (e.g., in the introns, control sequences, promoters) as these also lead to a dysfunction in the expressed protein. Such mutations may be single nuclear polymorphisms (SNPs).

The mutation may have the effect of decreasing binding between glypican and sclerostin. Compared with a healthy subject, the binding may be at least 10%, 20%, 30%, 40%, 50%, 60%, 70%, 80%, and preferably at least 20% lower than the binding observed in a healthy subject. Where a decrease in binding is observed, a disorder relating to high bone mass can be diagnosed or predicted.

The mutation may have the effect of increasing the signalling response of the Wnt and/or BMP pathways. Compared with a healthy subject, the signalling response may be at least 10%, 20%, 30%, 40%, 50%, 60%, 70%, 80%, and preferably at least 20% higher than the response observed in a healthy subject. Where an increase in response is observed, a disorder relating to high bone mass can be diagnosed or predicted.

Alternatively, the mutation may have the effect of increasing the binding between glypican and sclerostin. Compared with a healthy subject, the binding may be at least 10%, 20%, 30%, 40%, 50%, 60%, 70%, 80%, and preferably at least 20% higher than the binding observed in a healthy subject. Where an increase in binding is observed, a disorder relating to high bone mass can be diagnosed or predicted.

The mutation may have the effect of decreasing the signalling response of the Wnt and/or BMP pathways. Compared with a healthy subject, the signalling response may be at least 10%, 20%, 30%, 40%, 50%, 60%, 70%, 80%, and preferably at least 20% lower than the response observed in a healthy subject. Where an decrease in response is observed, a disorder relating to low bone mass can be diagnosed or predicted.

Binding and signalling assays are within the routine practices of the skilled person, and are described above. Methods of sequencing specific genes is well known and described, for example, in Sambrook et al., Molecular Cloning: A Laboratory Manual, Cold Spring Harbor Laboratory Press, New York (1989).

Glypican

By glypican as used herein, it is meant any glypican belonging to the glypican family, including functional portions and homologues thereof. There are presently identified six human glypicans, known as glypican-1 (Swiss-Prot accession no. P35052), glypican-2 (Swiss-Prot accession no. 08N158), glypican-3 (Swiss-Prot accession no. P51654), glypican-4 (Swiss-Prot accession no. 075487), glypican-5 (Swiss-Prot accession no. P78333), and glypican-6 (Swiss-Prot accession no. Q9Y625). It is preferably glypican-3.

The glypican as used herein may be purified from tissues, or more preferably, is recombinant glypican overexpressed in micro-organisms such as bacterial or yeast, or obtained by tissue culture. The preparation of recombinant glypican is known to the skilled person based on sequence information and common cloning techniques such as described in Sambrook et al., Molecular Cloning: A Laboratory Manual, Cold Spring Harbor Laboratory Press, New York (1989), and in Ausubel at al., Current Protocols in Molecular Biology, John Wiley and Sons, Baltimore, Md. (1989) and in Perbal, A Practical Guide to Molecular Cloning, John Wiley & Sons, New York (1988), and in Watson at al., Recombinant DNA, Scientific American Books, New York and in Birren et al (eds) Genome Analysis: A Laboratory Manual Series, Vols. 1-4 Cold Spring Harbor Laboratory Press, New York (1998) and methodology as set forth in U.S. Pat. Nos. 4,666,828; 4,683, 202; 4,801,531; 5,192,659 and 5,272,057 and incorporated herein by reference. Recombinant glypican may be provided with or without the carbohydrate or lipid moieties which are found in glypican purified from tissues.

Sclerostin

By sclerostin as used herein, it is meant any sclerostin belonging to the sclerostin family, including functional portions and homologues thereof. There is presently identified one human sclerostin, known as sclerostin (Swiss-Prot accession no. Q9BQB4).

The inventors have found that sclerostin comprises a SLIT-like domain which they believe is the element that interacts with glypican to inhibit Wnt and/or BMP signalling. Accordingly, sclerostin as used here can also include any protein having a SLIT-like domain. SLIT-like domain proteins are known in the art, for example, from Francesca Ronca, *J. Biol. Chem.*, (2001), Vol. 276, Issue 31, 29141-29147, incorporated herein by reference in its entirety.

The sclerostin as used herein may be purified from tissues, or more preferably, is recombinant sclerostin over-expressed in micro-organisms such as bacterial or yeast, or obtained by tissue culture. The preparation of recombinant sclerostin is known to the skilled person based on sequence information and common cloning techniques such as described in the references above. Recombinant sclerostin may be provided with or without the carbohydrate moieties which are found in sclerostin purified from tissues.

Homologous Sequence and Functional Portion

As used herein, a homologous sequence of the present invention may comprise additions, deletions or substitutions of one or more amino acids, which do not substantially alter the functional characteristics of polypeptide glypican or sclerostin) compared with the unmodified polypeptide. The functionality of the homologous sequence can be tested using the above mentioned binding and signalling assays. The number of amino acid deletions or substitutions is preferably up to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69 or 70 amino acids.

A homologous sequence according to the present invention may be a sequence which exists in other species such as, for example, mouse, rat, chicken etc.

Where homologous sequence indicates sequence identity, it means a sequence which presents a high sequence identity (more than 70%, 75%, 80%, 85%, 90%, 95% or 98% sequence identity) with the parent sequence and is preferably characterised by similar properties of the parent sequence, namely affinity, and said identity calculated using known methods.

As used herein, a functional portion refers to a smaller portion of a polypeptide (i.e., of glypican or sclerostin) of sufficient size and comprises sufficient functional groups such that the interaction of interest is at least 10% (or 20%, 30%, 40%, 50%, 60%, 70%, 80% 90%) of that of the parent polypeptide.

Alternatively, a functional portion comprises a partial deletion of the complete amino acid sequence and still maintains the binding site(s) and protein domain(s) necessary for the binding of and interaction with the target.

As used herein, a functional portion refers to less than 100% of the complete sequence (e.g., 99%, 90%, 80%, 70%, 60% 50%, 40%, 30%, 20%, 10%, 5%, 1% etc.), but comprises 5 or more amino acids.

Modifications to Inhibitor or Mimetic

The inhibitor or mimetic as described herein can be an inactive pre-cursor from which the active form is generated in vivo by enzymatic or other activities. It may also or alternatively be modified with the addition of functional groups or substances in order to increase the solubility, increase half-life, increase permeability through membranes, or to promote active uptake.

Inhibitors of the Sclerostin-Glypican Interaction

In preferred embodiments, an inhibitor of reducing or inhibiting the sclerostin-glypican interaction can be chosen from the group consisting of chemical substances, preferably an organic molecule, more preferably a small organic molecule; an antisense agent, e.g., an antisense oligonucleotide, a ribozyme, or an agent capable of causing RNA interference. In a preferred embodiment, an inhibitor of reducing or inhibiting the sclerostin-glypican interaction is an antisense reagent, esp. an antisense oligonucleotide.

The term "antisense" as used herein refers to a molecule designed to interfere with gene expression and capable of specifically binding to a desired target polynucleotide sequence, preferably coding for glypican or sclerostin. Antisense molecules typically (but not necessarily) comprise an oligonucleotide or oligonucleotide analogue capable of specifically hybridising to the target sequence. Hence, the term "antisense" oligo-nucleotide refers to an oligonucleotide or oligonucleotide analogue comprising, consisting essentially of or consisting of a nucleic acid sequence that is complementary or substantially complementary (i.e., largely but not wholly complementary) to a sequence within genomic DNA, hnRNA, mRNA or cDNA, preferably mRNA or cDNA, encoding a protein of interest; such as, e.g., within the genomic DNA, hnRNA, mRNA or cDNA, preferably mRNA or cDNA, of sclerostin or glypican. "Substantially complementary" refers to at least 85% complementary, e.g., preferably at least 90% complementary, e.g., at least 91% complementary, 92% complementary, more preferably at least 93% complementary, e.g., 94% complementary, even more preferably at least 95% complementary, e.g., at least 96% complementary, yet more preferably at least 97% complementary, e.g., at least 98% complementary, and most preferably at least 99% complementary. It is contemplated that antisense oligonucleotide may be complementary or substantially complementary to any of the 5' untranslated region, the coding region and/or the 3' untranslated region of an mRNA or cDNA.

Without being limited to any theory or mechanism, it is generally believed that the activity of antisense oligonucleotides depends on the binding of the oligonucleotide to the target nucleic acid, thus disrupting the function of the target, either by hybridization arrest (e.g., preventing the action of polymerases RNA processing) or by destruction of target RNA by RNase H (the ability to activate RNAse H when hybridised to RNA) resulting in inhibition of expression.

In this and below references, the terms "hybridisation" or "hybridise" as used herein, refers to any process by which a strand of nucleic acid binds with a strand comprising complementary sequence(s) through base pairing, preferably involving hydrogen bonding, more preferably by Watson-Crick base pairing interactions. Hybridisation can take place between distinct strands or within the same strand.

Hybridisation and the strength of hybridisation (i.e., the strength of the association between the nucleic acid strands) is impacted by such factors as the degree of complementary between the nucleic acids, stringency of the conditions involved, the melting temperature of the formed hybrid, and the G:C ratio within the nucleic acids. In addition to sequence information, it is possible to determine if a nucleic acid has $\geq 85$, $\geq 90$, $\geq 95$ or even $\geq 100\%$ identity/complementarity by hybridisation at high stringency. "High stringency" conditions include conditions equivalent to the following exemplary conditions for binding or hybridisation at 65° C. in a solution consisting of 5×SSPE (43.8 g/l NaCl, 6.9 g/l $NaH_2PO_4 \cdot H_2O$ and 1.85 g/l EDTA, pH adjusted to 7.4 with NaOH), 0.1% SDS, 5×Denhardt's reagent (50×Denhardt's contains per 500 ml: 5 g Ficoll (Type 400, Pharmacia), 5 g BSA (Fraction V; Sigma) and 100 µg/ml denatured salmon sperm DNA), followed by washing in a solution comprising 5×SSPE, 0.1% SDS at 65° C. when a probe of about 500 nucleotides in length is employed. Other exemplary conditions for hybridisation at "high stringency" for nucleic acid sequences over approximately 50-100 nucleotides in length include conditions equivalent to hybridisation in 6×SSC at 45° C., followed by one or more washes in 0.2×SSC, 0.1% SDS at 65° C. Numerous equivalent conditions may be employed to vary stringency conditions; factors such as the length and nature (DNA, RNA, base composition) of the probe and nature of the target (DNA, RNA, base composition, present in solution or immobilised, etc.) and the concentration of the salts and other components (e.g., the presence or absence of formamide, dextran sulphate, polyethylene glycol) are considered and the hybridisation solution may be varied to generate conditions of low or high stringency hybridisation different from, but equivalent to, the above listed conditions. In addition, the art knows conditions that promote hybridisation under conditions of high stringency (e.g., increasing the temperature of the hybridisation and/or wash steps, the use of formamide in the hybridisation solution, etc.). Guidance for performing hybridisation reactions can be found, for example, in Current Protocols in Molecular Biology, John Wiley & Sons, N.Y., 6.3.1-6.3.6, 1989, and more recent updated editions, all of which are incorporated by reference.

Typically, antisense agents suitable for the present invention may be capable of hybridising to their respective target at high stringency conditions. Such agents may hybridise specifically to the target under physiological conditions.

The terms "complementary" or "complementarity" as used herein with reference to nucleic acids, refer to the normal binding of polynucleotides under permissive salt (ionic strength) and temperature conditions by base pairing, preferably Watson-Crick base pairing. By means of example, complementary Watson-Crick base pairing occurs between the bases A and T, A and U or G and C. Complementarity between two single-stranded nucleic acid molecules may be "partial", such that only some nucleotides of the nucleic acids would bind when the strands hybridise, or it may be "complete", such that total complementarity exists between the single stranded molecules. By means of example, a relatively shorter nucleic acid strand would show total complementarity to a relatively longer nucleic acid strand, if the latter strand comprised a sequence fully complementary to the sequence of the former strand. The "degree of complementarity" of a nucleic acid molecule (1) to a nucleic molecule (2) can be expressed as the proportion (percentage) of nucleotides of the nucleic acid (1) molecule that would be expected to match, i.e., form Watson-Crick base-pairing, with nucleotides of the nucleic acid molecule (2), when the said nucleic acid molecules (1) and (2) were hybridised, preferably in high stringency conditions.

In a further preferred embodiment, an inhibitor capable of reducing or inhibiting the sclerostin-glypican interaction is a ribozyme.

The term "ribozyme" as used herein refers to a nucleic acid molecule, preferably an oligonucleotide or oligonucleotide analogue, capable of catalytically cleaving a polynucleotide. Preferably, a "ribozyme" may be capable of cleaving mRNA of a given polypeptide or protein, thereby reducing translation thereof; such as, preferably mRNA of glypican or sclerostin. Exemplary ribozymes contemplated herein include, without limitation, hammer head type ribozymes, ribozymes of the hairpin type, delta type ribozymes, etc. For teaching on ribozymes and design thereof, see, e.g., U.S. Pat. No. 5,354,855, U.S. Pat. No. 5,591,610, Pierce et al. 1998 (Nucleic Acids Res 26: 5093-5101), Lieber et al. 1995 (Mol Cell Biol 15: 540-551), and Benseler et al. 1993 (J Am Chem Soc 115: 8483-8484), incorporated herein by reference in their entirety.

In a yet further preferred embodiment, an inhibitor capable of reducing or inhibiting the sclerostin-glypican interaction is competent of causing RNA interference with the respective transcripts, preferably mRNAs.

"RNA interference" or "RNAi" is a term initially applied to a phenomenon observed in plants and worms where double-stranded RNA (dsRNA) blocks gene expression in a specific and post-transcriptional manner. Consequently, RNAi refers generally to the process of sequence-specific post-transcriptional gene silencing in animals mediated by short interfering nucleic acids (siNA), preferably by short interfering RNAs (siRNAs). RNAi provides a useful method of inhibiting gene expression in vitro or in vivo.

RNA interference agents may include any of short interfering nucleic acid (siNA), short interfering RNA (siRNA), double-stranded RNA (dsRNA), micro-RNA (miRNA), and short hairpin RNA (shRNA) molecules capable of mediating RNA interference (RNAi) against the expression of sclerostin or glypican.

In the present context, the expression "dsRNA" relates to double stranded RNA capable of causing RNA interference. In accordance with the present invention, any suitable double-stranded RNA fragment capable of directing RNAi or RNA-mediated gene silencing of a target gene can be used. As used herein, a "double-stranded ribonucleic acid molecule (dsRNA)" refers to any RNA molecule, fragment or segment containing two strands forming an RNA duplex, notwithstanding the presence of single stranded overhangs of unpaired nucleotides. The double-stranded RNA comprises annealed complementary strands, one of which has a nucleotide sequence which corresponds to a target nucleotide sequence (i.e. to at least a portion of the mRNA transcript) of the target gene to be down-regulated. The other strand of the double-stranded RNA is complementary to this target nucleotide sequence.

The double-stranded RNA need only be sufficiently similar to the mRNA sequence of the target gene to be down-regulated that it has the ability to mediate RNAi. Thus, the invention has the advantage of being able to tolerate sequence variations that might be expected due to genetic mutation, strain polymorphism or evolutionary divergence. The number of tolerated nucleotide mismatches between the target sequence and a nucleotide sequence of the dsRNA sequence is no more than 1 in 5 basepairs, or 1 in 10 basepairs, or 1 in 20 basepairs, or 1 in 50 basepairs. According to the invention, the "dsRNA" or "double stranded RNA", whenever said expression relates to RNA that is capable of causing interference, may be formed form two separate (sense and antisense) RNA strands that are annealed together. Alternatively, the dsRNA may have a foldback stem-loop or hairpin structure wherein the two annealed strands of the dsRNA are covalently linked. In this embodiment, the sense and anti-sense strands of the dsRNA are formed from different regions of a single RNA sequence that is partially self-complementary.

As used herein, the term "RNAi molecule" is a generic term referring to double stranded RNA molecules including small interfering RNAs (siRNAs), hairpin RNAs (shRNAs), and other RNA molecules which can be cleaved in vivo to form siRNAs. RNAi molecules can comprise either long stretches of dsRNA identical or substantially identical to the target nucleic acid sequence or short stretches of dsRNA identical or substantially identical to only a region of the target nucleic acid sequence.

The subject RNAi molecules can be "small interfering RNAs" or "siRNAs." siRNA molecules are usually synthesized as double stranded molecules in which each strand is around 19-30 nucleotides in length, and even more preferably 21-23 nucleotides in length. The siRNAs are understood to recruit nuclease complexes and guide the complexes to the target mRNA by pairing to the specific sequences. As a result, the target mRNA is degraded by the nucleases in the protein complex. In a particular embodiment, the siRNA molecules comprise a 3' hydroxyl group. In certain embodiments, the siRNA molecules can be generated by processing of longer double-stranded RNAs, for example, in the presence of the enzyme dicer.

Alternatively, the RNAi molecule is in the form of a hairpin structure, named as hairpin RNA or shRNA. The hairpin RNAs can be synthesized exogenously or can be formed by transcribing from RNA polymerase III promoters in vivo. Preferably, such hairpin RNAs are engineered in cells or in an animal to ensure continuous and stable suppression of a desired gene. It is known in the art that siRNAs can be produced by processing a hairpin RNA in the cell.

The present RNAi molecules may include modifications to either the phosphate-sugar backbone or the nucleoside, e.g., to reduce susceptibility to cellular nucleases, improve bioavailability, improve formulation characteristics, and/or change other pharmacokinetic properties.

In some cases, at least one strand of the RNAi molecules has a 3' overhang from about 1 to about 6 nucleotides in length, and for instance from 2 to 4 nucleotides in length. More preferably, the 3' overhangs are 1-3 nucleotides in length. In certain embodiments, one strand has a 3' overhang and the other strand is blunt-ended or also has an overhang. The length of the overhangs may be the same or different for each strand. In order to further enhance the stability of the RNAi molecules, the 3' overhangs can be stabilized against degradation. In one embodiment, the RNA is stabilized by including purine nucleotides, such as adenosine or guanosine nucleotides. Alternatively, substitution of pyrimidine nucleotides by modified analogues, e.g., substitution of uridine nucleotide 3' overhangs by 2'-deoxythymidine is tolerated and does not affect the efficiency of RNAi. For further details on design of siRNA agents, see, e.g., Elbashir et al. 2001 (Nature 411: 494-501), which is incorporated by reference.

In a preferred embodiment, the invention relates to the use of an RNA sequence to prepare an RNAi molecule as defined herein, and preferably a siRNA molecule. Said siRNA molecule is characterized by one or more, and preferably by all of the following criteria:

having at least 50% sequence identity, preferably at least 70% sequence identity, more preferred at least 80% sequence identity, even more preferred at least 90% sequence identity with the target mRNA, e.g., mRNA for sclerostin or glypican;

having a sequence which targets the exon area of the target gene;

showing a preference for targeting the 3' end of the target gene rather than for targeting the 5' end of the target gene.

In a further preferred embodiment, the siRNA molecule may be further characterized by one or more of the following criteria:
- having a nucleic acid length of between 15 to 25 nucleotides and preferably of between 18 to 22 nucleotides, and preferably of 19 nucleotides;
- having a GC content comprised between 30 and 50%
- showing a TT(T) sequence at its 3' end;
- showing no secondary structure when adopting the duplex form; and/or
- having a Tm (melting temperature) of lower than 20° C.

Production of any above nucleic acid reagents, including antisense reagents, ribozymes and RNAi molecules, can be carried out by chemical synthetic methods or by recombinant nucleic acid techniques, e.g., expressed from a vector in a cell, e.g., a viral vector, a eukaryotic expression vector, a gene therapy expression vector (i.e., in vivo), etc., or enzymatically synthesized, e.g., by in vitro transcription from a DNA template using a T7 or SP6 RNA polymerase. The nucleic acid molecules may be produced enzymatically or by partial/total organic synthesis. Any modified ribonucleotide can be introduced by in vitro enzymatic or organic synthesis.

Any of the above nucleic acid reagents, including antisense reagents, ribozymes and RNAi molecules, can be purified using a number of techniques known to those of skill in the art. For example, gel electrophoresis can be used to purify nucleic acid reagents. Alternatively, non-denaturing methods, such as non-denaturing column chromatography, can be used to purify the molecules. In addition, chromatography (e.g., size exclusion chromatography), glycerol gradient centrifugation, affinity purification with antibody can be used to purify the molecules.

It is realized that the main obstacle to achieve in vivo gene silencing by nucleic acids, e.g., antisense, ribozyme or RNAi technologies, is delivery. To improve thermal stability, resistance to nuclease digestion and to enhance cellular uptake of such tools, various approaches are applicable and are known to a skilled person. They include, e.g.:
- chemical modifications like locked nucleic acid (LNA), phosphonate substitution, phosphorothioate substitution, phosphorodithioate substitution, morpholino oligomers, 2'-fluoro substitution, 2'-O-methyl substitution, stabilized Stealth™ RNAi (Invitrogen), etc.
- encapsulation in various types of liposomes (immunoliposomes, PEGylated (immuno) liposomes), cationic lipids and polymers, nanoparticules or dendrimers, poly (lactic-Co-Glycolic Acid) polymeric microspheres, implantable drug-releasing biodegradable microspheres, etc.;
- co-injection with protective agent such as the nuclease inhibitor aurintricarboxylic acid.

Nevertheless, as detailed in the examples, delivery of expression vectors and naked RNAi by electroporation was extremely successful.

Composition

A composition as described herein may be a pharmaceutical composition. The invention provides for compositions comprising an inhibitor or glypican mimetic according to the invention admixed with a physiologically compatible carrier. As used herein, "physiologically compatible carrier" refers to a physiologically acceptable diluent such as water, phosphate buffered saline, or saline.

The invention also provides for pharmaceutical compositions. In addition to the active ingredients, these pharmaceutical compositions may contain suitable pharmaceutically acceptable carrier preparations which can be used pharmaceutically.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethyl-cellulose, or sodium carboxymethyl cellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterise the quantity of active compound, i.e., dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilisers.

Pharmaceutical formulations for parenteral administration include aqueous solutions of active compounds. For injection, the pharmaceutical compositions of the invention may be formulated in aqueous solutions, preferably in physiologically compatible buffers such as Hank's solution, Ringer' solution, or physiologically buffered saline. Aqueous injection suspensions may contain substances which increase the viscosity of the suspension, such as sodium carboxymethyl cellulose, sorbitol, or dextran. Additionally, suspensions of the active solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For nasal administration, penetrants appropriate to the particular barrier to be permeated are used in the formulation. Such penetrants are generally known in the art.

The pharmaceutical compositions of the present invention may be manufactured in a manner known in the art, e.g. by means of conventional mixing, dissolving, granulating, dragee-making, levitating, emulsifying, encapsulating, entrapping or lyophilizing processes.

The pharmaceutical composition may be provided as a salt and can be formed with many acids, including but not limited to hydrochloric, sulphuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

After pharmaceutical compositions comprising a compound of the invention formulated in an acceptable carrier have been prepared, they can be placed in an appropriate container and labelled for treatment of an indicated disorder with information including amount, frequency and method of administration.

The above mentioned substances for use in a composition may be included, where appropriate in a vaccine according to the present invention.

Administration

The compositions, vaccines and methods described herein are administered according to known pharmaceutical methods and techniques. The composition or vaccine of the present invention is administered and dosed in accordance with good medical practice, taking into account the clinical disorder of the individual patient, the site and method of administration, scheduling of administration, patient age, sex, body weight and other factors known to medical practitioners. The pharmaceutically "effective amount" for purposes herein is thus determined by such considerations as are known in the art and as described herein.

The composition or vaccine of the present invention may be administered intrathecally. Intrathecal administration is advantageous because this route largely bypasses the blood-brain barrier. Further, by providing a high local concentration of the composition, toxicity can be reduced or eliminated, which could result from systemic administration in high enough doses to achieve the required concentration. Intrathecal administration can occur by any manner known by those of skill in the art. For example, intrathecal delivery can occur through an implanted depot of collagen (Hamann, et al., 2003) or other biocompatible, biodegradable, injectable, and fast gelling biomaterial (e.g. hyaluronan) known to those of skill in the art. Such implanted material provide for higher drug concentrations. A more specific example of a hyaluronan is a high molecular weight divinylsulfone cross-linked hyaluronan preparation. The degree of cross-linking of this hyaluronan preparation is about 1/20 monosaccharide residues, and at equilibrium hydration it has a polysaccharide concentration of ~0.5%. Although it appears to be a solid gel, the actual slurry of gel particles is very plastic (e.g., can be extruded through a 30 gauge needle) and can stay in place for adequate periods (days to weeks).

In the method of the present invention, the composition or vaccines of the present invention can be administered in various ways.

The compositions can be administered orally, subcutaneously or parenterally including intravenous, intra-arterial, intramuscular, intraperitoneally, and intranasal administration as well as intrathecal and infusion techniques. The vaccines can be administered subcutaneously or parenterally including intravenous, intra-arterial, intramuscular, intraperitoneally, and intranasal administration as well as intrathecal and infusion techniques. Implants of the compositions or vaccines are also useful. For example, implants can be a depot of collagen (Hamann, et al., 2003) or other biocompatible, biodegradable, injectable, and fast gelling biomaterial (e.g. hyaluronan) known to those of skill in the art. The patient being treated is a warm-blooded animal and, in particular, mammals including man.

When administering the composition or vaccine of the present invention parenterally, it can generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Non-aqueous vehicles such a cottonseed oil, sesame oil, olive oil, soybean oil, corn oil, sunflower oil, or peanut oil and esters, such as isopropyl myristate, can also be used as solvent systems for compound compositions. Additionally, various additives which enhance the stability, sterility, and isotonicity of the compositions, including antimicrobial preservatives, antioxidants, cheating agents, and buffers, can be added. Prevention of the action of micro-organisms can be ensured by various antibacterial and antifungal agents, for example, parabens, chlorobutanol, phenol, sorbic acid, and the like. In many cases, it can be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used is compatible with the composition or vaccine of the present invention.

Sterile injectable solutions can be prepared by incorporating the compositions or vaccines utilized in practicing the present invention in the required amount of the appropriate solvent with several other ingredients, as desired.

A pharmacological formulation of the present invention can be administered to the patient in an injectable formulation containing any compatible carrier, such as various vehicle, additives, and diluents; or the compositions utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include the systems described in U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

A pharmacological formulation of the composition utilised with the present invention can be administered orally to the patient. Conventional methods such as administering the compositions in tablets, suspensions, solutions, emulsions, capsules, powders, syrups and the like are usable. Known techniques, which deliver it orally or intravenously and retain the biological activity, are preferred.

In one embodiment, the composition or vaccine of the present invention can be administered initially by intravenous injection to bring blood levels to a suitable level.

Dose

It is noted that humans can be treated longer than the mice or other experimental animals exemplified herein, which treatment has a length proportional to the length of the disease process and drug effectiveness. The doses can be single doses or multiple doses over a period of several days, but single doses are preferred. The treatment generally has a length proportional to the length of the disease process and drug effectiveness and the patient species being treated.

The quantity to be administered can vary for the patient being treated, and can vary from about 100 ng/kg of body weight to 100 mg/kg of body weight per day and preferably can be from 1 mg/kg to 10 mg/kg per day.

EXAMPLES

The above discussion provides a factual basis for the use of the present invention described herein. The methods used with a utility of the present invention can be shown by the following non-limiting examples.

Example 1

Sclerostin Inhibits BMP-Induced Bone Formation In Vivo

To investigate the effect of sclerostin on BMP-stimulated bone formation in vivo, the effect on BMP-induced bone formation was studied in tibial muscle of mice using electroporation to induce expressing of BMP and/or sclerostin, essentially as described by Cichon et al. (2002, Cancer Gene Therapy 9:771-777; Electrotransfer of gene encoding endostatin into normal and neoplastic mouse tissues: Inhibition of primary tumor growth and metastatic spread) and as further detailed by Molnar et al. (2004, Molecular Therapy 10: 447-455). In short, a control construct consisting of an empty construct; a BMP-7 expression construct and a Sclerostin expression construct (SOST) were used. The gastrocnemius muscles of the mice were injected with hyaluronidase about 2 h prior to plasmid injection. The voltage and duration of the pulse was optimized experimentally. The constructs were electroporated as naked DNA. The animals were anesthetized before electroporation. The following experimental settings were used: (A) control; (B) BMP; (C) SOST; and (D) BMP+SOST, i.e. BMP-7 expression construct together with a Sclerostin expression construct in a ratio of 1:1.

BMP induced bone formation in the muscle as seen on X-rays 14 days after electroporation. The bone formed, showed normal histology, contained bone marrow, and may be connected to the fibula and/or tibia. Sclerostin expression itself did not induce bone formation in the muscle nor did induce any histological changes in the muscle. Co-electroporation of BMP with sclerostin, however, completely prevented BMP-induced bone formation essentially as described in van Bezooijen et al., (2007) [Wnt but Not BMP Signaling Is Involved in the Inhibitory Action of Sclerostin on BMP-Stimulated Bone Formation., J Bone Miner Res. 2007 January; 22(1):19-28].

Example 2

Micro-Array Analysis

Micro-array analysis was performed to gain insight into the mechanism by which sclerostin may inhibit BMP-stimulated bone formation. For this, confluent mouse osteoblastic KS384 cells were treated for 6 hours with BMP and/or sclerostin. Of note, these osteoblastic cells produce endogenous BMPs that are biologically active. BMP affected the expression of 2069 probe sets of which 74% was upregulated and 26% downregulated. Sclerostin affected 1828 probe sets of which 18% was upregulated and 82% downregulated. 408 Probe sets were affected by both BMP and sclerostin; 20% and 22% of the BMP and sclerostin-affected probe sets, respectively. Of these probe sets, 65% showed an opposite effect for BMP and sclerostin, as expected for an agonist and its classical antagonist that prevents binding of the BMPs to their receptors. However, the other 35% of probe sets were affected by BMP and sclerostin in the same direction. In addition, the combination of BMP and sclerostin affected 1051 probe sets differently from the cumulative effect of BMP and sclerostin alone (data not shown). The two latter findings suggest that sclerostin may do something else than antagonizing BMP signaling.

To address the antagonistic effect of sclerostin on BMP signaling directly, the expression of proven direct BMP target genes was checked and, as expected, BMP increased their expression levels. Sclerostin, however, did not affect their expression; except for CTGF and Msx-2 that were downregulated. The combination of BMP and sclerostin did not effect the stimulated expression of the BMP target genes different from the cumulative effect of BMP and sclerostin alone; only the BMP-stimulated expression of the Id genes was further increased by sclerostin. The latter may indicate that sclerostin removes a suppressor of BMP-stimulated expression of Id genes. Together these findings further support the observation that sclerostin is not a classical BMP antagonist.

In order to determine the mechanism by which sclerostin inhibits BMP-stimulated bone formation in an unbiased way, a functional analysis based upon Gene Ontology (GO)-terms was performed, i.e., groups of probes sets with a common characteristic. In this analysis, an enrichment of affected probe sets within a GO-term suggests that it is affected by the treatment. The GO-database contains 5441 GO-terms of which 35 contain probes sets correlated with a specific growth factor pathway. These GO-terms for specific pathways can be used to identify the signaling pathway(s) affected by sclerostin that may account for its inhibitory effect on BMP-stimulated bone formation. BMP enriched 443 (8%) GO-terms. Of these enriched GO-terms, three GO-terms represented the two signaling pathways transforming growth factor beta (TGF-β) and Notch. This suggests that BMP affects its own and the Notch signaling pathway; two well known effects of BMP stimulation.

Sclerostin enriched 389 (7%) GO-terms, among which three represented the two signaling pathways Wnt and TGF-beta. The combination BMP and sclerostin enriched the presence of probe sets affected differently from the cumulative effect of BMP and sclerostin alone in 296 (5%) GO-terms. Three GO-terms represented the two signaling pathways BMP and platelet-derived growth factor (PGDF).

In a similar approach using KEGG (Kyoto Encyclopedia of Genes and Genomes) pathway analysis, BMP was found to significantly enrich the number of affected probe sets in 22 (11%) KEGG pathways out of a total of 204 KEGG pathways. One out of the enriched KEGG pathways represented the TGF-β signaling pathway. Sclerostin enriched 20 (10%) of the KEGG pathways among which two represented the TGF-β signaling pathway and the Wnt signaling pathway. The combination BMP and sclerostin enriched the presence of probe sets affected differently from the cumulative effect of BMP and sclerostin alone in 16 (8%) KEGG pathways among which one represented the Wnt signaling pathway. An important restriction of the KEGG-database for this kind of analysis is, however, that it contains only 5 KEGG pathways specific for a certain growth factor, i.e., Wnt, Notch, hedgehog, TGF-β, and insulin. Together the GO and KEGG analysis indicate that sclerostin is most likely to affect either TGF-beta/BMP signaling or Wnt signaling.

Example 3

Sclerostin does not Antagonize BMP Signaling

Analysis of the direct BMP target genes suggested that sclerostin is not a classical BMP antagonist and this was in line with the observations that sclerostin did not antagonize early BMP responses like Smad phosphorylation and BMP reporter construct activation. These observations are restricted to one cell line and it may be possible that sclerostin antagonizes BMP signaling in other cells depending on the cellular context. Winkler et al., for example, reported that sclerostin partly inhibited BMP-stimulated Smad phosphorylation in mouse mesenchymal C3H10T1/2 cells. To look for cell line specific effects of sclerostin on BMP signaling, three other osteoblastic cell lines including C3H10T1/2 cells were tested, using an experimental set-up essentially as described in van Bezooijen et al., (2007). In particular, BRE-luc transfected C3H10T1/2 cells were stimulated with sclerostin (5 μg/ml), BMP4 (3 ng/ml), or BMP4+sclerostin for 24 hours after which BRE-luc activity was measured. BRE-luc transfected UMR106 cells were treated as described above, but BMP4 concentration was 100 ng/ml. BRE-luc transfected U2OS cells were treated as described above, but BMP4 concentration was 10 ng/ml. In addition, cells were stimulated for 24 hours with noggin (200 ng/ml) or BMP4+noggin. Sclerostin, however, did not antagonize BMP-stimulated BMP reporter construct activation in any of the cell lines, while noggin did.

Sclerostin, however, may still antagonize BMP-stimulated bone formation by acting as a direct BMP antagonist late during BMP stimulation (hypothesis I: Sclerostin inhibits BMP-stimulated ALP activity by antagonizing BMP signaling late during BMP stimulation, for example, after induction of a co-factor required for sclerostin to act as a direct BMP antagonist). To investigate this, studies were performed to find out whether addition of sclerostin 24 hours after BMP stimulation inhibited BRE-luc activity, as it inhibited BMP-stimulated ALP activity. KS483 cells were stimulated with BMP4 (50 ng/ml) for 48 hours and sclerostin (5 μg/ml) or noggin (500 ng/ml) was added during the last 24 hours of culture. BRE-luc activity was measured 48 hours after BMP4 stimulation. The experiment was repeated similar to above, but BMP4 stimulation was for 72 hours and sclerostin or noggin was added during the last 48 hours of culture. Late addition of sclerostin to BMP-stimulated cultures, however, did not inhibit BRE-luc activity measured after 48 and 72 hours, in marked contrast to the classical BMP antagonist noggin. This showed that sclerostin did also not antagonise direct BMP responses late during BMP stimulation. Noggin did not completely antagonise BMP-stimulated BRE-luc activity measured 48 hours after BMP-stimulation, suggesting residual BRE-luc activity from the first 24 hours of BMP stimulation in the absence of noggin.

To further substantiate this issue, an experimental set-up was used in which the effect of sclerostin on a second pulse of BMP stimulation was studied using BRE-luc as readout. First, studies were performed to find out whether BRE-luc activity was restored to control level after the first BMP stimulation and removal of BMP stimulus. For this, BRE-luc transfected cells were pretreated with BMP4 (50 ng/ml) for 48 hours. Medium was changed to remove BMP stimulus for 24 hours before a second BMP4 (50 ng/ml) stimulation for 24 hours. BRE-luc activity was measured at 48, 72, and 96 hours after first BMP4 stimulation. KS483 cells were treated for 48 hours with BMP, which significantly increased BRE-luc activity.

Removal of BMP stimulus by changing culture medium restored BRE-luc activity to almost control levels after 24 hours and activity was further decreased to control level during the subsequent 24 hours. Specifically, cells were pretreated with BMP4 (50 ng/ml) for 48 hours. Medium was changed to remove BMP stimulus for 24 hours before cells were again stimulated with BMP4 (50 ng/ml), sclerostin (5 μg/ml), or BMP4+sclerostin for 24 hours. BRE-luc activity was measured 96 hours after first BMP4 stimulation. A second BMP stimulation 24 hours after medium change induced a renewed activation of BRE-luc. Although the second response was lower, it showed that it was possible to study the effect of sclerostin on a direct BMP response after prior BMP stimulation without the problem of residual BRE-luc activity. The second BMP-stimulated activation of BRE-luc was, however, also not antagonized by sclerostin. These results have been corroborated by the study by van Bezooijen et al. (2007).

Example 4

Sclerostin Antagonizes BMP-Stimulated Wnt Signaling

The GO and KEGG analysis suggested that sclerostin affects Wnt signaling. Wnts are suitable candidates for the yet unknown ligand targeted by sclerostin that cooperates with BMPs to induce bone formation (Hypothesis II: Sclerostin inhibits BMP-stimulated ALP activity by antagonizing another signaling pathway that cooperates with BMP in its response), since they have been reported to cooperate with BMPs to stimulate bone formation (Westendorf, 2004). To investigate whether Wnts play a role in BMP-stimulated ALP activity in KS483 cells, the effect of the Wnt antagonist Dkk1 was tested. Specifically, confluent KS483 cells were stimulated with BMP4 (50 ng/ml) in the absence or presence of a dose range of sclerostin (0.1-10 μg/ml). Moreover, cells were treated as described above, but in the absence or presence of a dose range of Dkk1 (1-1000 ng/ml). It was found that it inhibited BMP-stimulated ALP activity similar to sclerostin. In addition, a further experiment with TBE-luc transfected KS483 cells stimulated with a dose range of BMP4 (1-300 ng/ml) for 24 hours, demonstrate a BMP dose-dependently stimulation of the Wnt reporter construct TBE-luc. The array data suggest that BMP may stimulate Wnt signaling by increasing Wnt receptor expression, since the levels for Frizzled 1 and 7 were significantly upregulated by BMP, while of the Wnts only Wnt2 was upregulated (data not shown).

The cells were then stimulated with BMP in the absence or presence of the classical Wnt antagonist Dkk1 or sclerostin. Specifically, TBE-luc transfected cells were stimulated with BMP4 (50 ng/ml), BMP4+Dkk1 (1 μg/ml), or BMP4+sclerostin (5 μg/ml) for 24 hours. It was found that both antagonised BMP-stimulated TBE-luc activation. Since exogenously added BMPs are still present in this culture system and, therefore, an effect of sclerostin on these BMPs could not be excluded, studies were performed to find out whether sclerostin also antagonised activation of TBE-luc by constitutive active BMP type I receptors (caALK2 and caALK6) that signal independent of ligand. Similar to the effect on exogenously added BMPs, sclerostin antagonized activation of TBE-luc by both caALK2 and caALK6, as shown by cells co-transfected with TBE-luc and either caALK2 or caALK6 and cultured for 24 hours in absence or presence of sclerostin (5 µg/ml). Together these data suggest that sclerostin inhibits late BMP responses akin to ALP activity by antagonising Wnt signaling.

Example 5

Sclerostin Antagonises Wnt Signaling

To address the question whether sclerostin antagonizes Wnt signaling directly, studies were performed to find out whether sclerostin antagonised rmWnt3a-induced TBE-luc activity in KS483 cells. In particular, TBE-luc transfected KS483 cells were stimulated with, sclerostin (5 µg/ml), rmWnt3a (20 ng/ml), rmWnt3a+sclerostin, or rmWnt3a+ Dkk1 (10-1000 ng/ml) for 24 hours. Sclerostin, however, did not antagonise rhWnt3a-stimulated activation of this construct, while Dkk1 antagonized it dose-dependently.

Sclerostin, however, may only antagonize direct Wnt responses late during BMP stimulation, for example, after induction of a co-factor. Therefore, experiments were performed to test whether sclerostin antagonised rmWnt3a-induced TBE-luc activation after a pre-treatment with BMP. First, studies were performed to find out whether TBE-luc activity induced by BMP stimulation for 48 hours was restored to control level 24 hours after removal of the BMP stimulus by medium change. Specifically, cells were either not stimulated or stimulated with BMP4 (50 ng/ml) for 48 hours. TBE-luc activity was measured after 48 hours or after an additional 24 hours in which the cultures were either prolonged, removed of BMP stimulus by medium change, or stimulated with rmWnt3a (20 ng/ml) in the absence or presence of BMP stimulus. This was the case. Interestingly, TBE-luc activity was also restored to control level 72 hours after BMP stimulation without any medium change, i.e., still in the presence of BMP stimulus. rmWnt3a induced TBE-luc activity to a similar extend in untreated and BMP pre-treated cells, independent of a medium change after 48 hours of BMP stimulation. In particular, TBE-luc activity was measured 72 hours after transfection in non-stimulated or BMP4-stimulated (50 ng/ml) cells or cells stimulated with BMP4 for 48 hours followed by a stimulation with rmWnt3a (20 ng/ml), sclerostin (5 µg/ml), or rmWnt3a+sclerostin with or without medium change. This showed that is was possible to study the effect of sclerostin on rhWnt3a-induced TBE-luc activity after 48 hours pre-treatment with BMP. Sclerostin, however, did also not antagonise rhWnt3a-induced TBE-luc activity after 48 hours pre-treatment with BMP. This was again independent of medium change after 48 hours.

It may be, however, that sclerostin does not antagonise Wnt3a, but antagonizes other Wnts. Therefore, studies were performed to investigate whether sclerostin antagonised TBE-luc activity induced by co-transfection with an expression vector for Wnt1 or Wnt3. In addition, an expression vector for Wnt3a was used as comparison for stimulation with rmWnt3a. Specifically, KS483 cells were co-transfected with TBE-luc and expression constructs for Wnt1, Wnt3, or Wnt3a in the absence or presence of sclerostin (0.1-5 µg/ml) or Dkk1 (1 µg/ml). TBE-luc activity was measured 24 hours after transfection. Sclerostin completely antagonized Wnt1-induced TBE-luc activity and partly antagonized Wnt3-induced TBE-luc activity. Remarkably, sclerostin also antagonised TBE-luc activity induced by co-transfection with a Wnt3a expression vector. This suggests that exogenous added rmWnt3a and Wnt3a produced by transfected cells are both biological active, but differently recognized by sclerostin. Dkk1 antagonized TBE-luc activity induced by all three Wnt expression vectors as expected.

In conclusion, sclerostin inhibits ALP bone formation by a mechanism different from antagonising direct BMP signalling, which distinguishes sclerostin from classical BMP antagonists such as noggin. Sclerostin antagonised BMP-stimulated Wnt signalling in osteoblastic cells, suggesting that sclerostin inhibits BMP stimulated bone formation indirectly via antagonising Wnt signalling. Indeed, sclerostin antagonised direct Wnt1, Wnt3, and Wnt3a-stimulated Wnt reporter construct activation. Sclerostin, however, did not antagonise rmWnt3a-stimulated Wnt reporter construct activation, while Dkk1 did. This distinguishes sclerostin's mechanism of action from that of the Wnt antagonist Dkk1. Together these findings indicate that sclerostin, secreted by osteocytes, inhibits BMP-stimulated bone formation by antagonising Wnt signalling in osteoblasts. High bone mass in sclerosteosis and van Buchem disease may, therefore, result from increased Wnt signalling due to the absence of sclerostin. This raises the possibility that the skeletal disorders, sclerosteosis, van Buchem disease, and the human high bone mass phenotype are due to increased activity of one and the same signalling pathway. In HBM, incapability of Dkk1 to inhibit Wnt signalling increases bone formation, while in sclerosteosis and van Buchem disease this is due to the absence of sclerostin-inhibited Wnt signalling.

Example 6

Sclerostin Binds Glypican

In order to further delineate the mechanism by which sclerostin inhibits ALP bone formation, we investigated potential binding partners for sclerostin. We hypothesized that the SLIT-domain of sclerostin may potentially be involved in binding. A HybriZAP two-hybrid screen system in yeast cells is performed for cDNA screening according to the manufacture's instructions (Stratagene), using sclerostin as bait. The prey cDNA libraries used are those constructed from a mixture of random- and oligo(dT)-primed cDNAs of poly(A)$^+$ RNAs isolated from 17-day embryo and adult mouse cells. The HybriZAP phage cDNA library is amplified and converted to a pAD-gal4 plasmid library by helper phage-aided in vivo mass excision. Yeast transformants carrying each prey plasmid are generated, and the pAD-gal4 plasmid cDNA library is used for two-hybrid screening. Colonies are selected by histidine prototrophy in the presence of 3-aminotriazole (3-AT) and by expression of UAS-lacZ. Plasmid DNAs of the selected colonies are recovered and transformed into *Escherichia coli* to isolate the prey cDNA clones. The prey-bait interaction is confirmed by transforming a second yeast strain with the isolated bait and prey plasmids and examining for histidine prototrophy and fl-galactosidase expression. After isolation and sequencing, the prey is identified as Glypican.

Northern blot analysis with glypican probes confirms the expression of Glypican in various bone and bone progenitor cells.

6.1. Immunoprecipitation Assays

Binding between sclerostin and glypican is confirmed by an in vitro binding assay. In short, GST (glutathione S-transferase) fusion proteins of glypican are expressed in *E. coli* cells, using pGEX-4T-1 vector (Pharmacia), and are subsequently purified. Sclerostin tagged with Xpress sequence at its N terminus is synthesized in vitro, using pcDNA 3.1 vector (Invitrogen) and the TNT coupled rabbit reticulocyte lysate system (Promega). Thirty microliters of reticulocyte lysate containing the synthesized protein is added to 250 µl of the glutathione-Sepharose beads which are bound with GST or GST-CtBP1/2 suspended in TPBS (phosphate-buffered saline with 1% Tween 20) containing 0.01% bovine serum albumin and which are kept at 4° C. for 1 h with gentle mixing. The beads are washed extensively with 0.01% bovine serum alin-TPBS; the bound protein is released by boiling in sodium dodecyl sulfate-containing sample buffer for polyacrylamide gel electrophoresis and subjected to Western blotting using anti-Xpress antibody (Invitrogen). The results demonstrate that sclerostin co-precipitates with Glypican. Thus, sclerostin binds to glypican.

In order to confirm the interaction between sclerostin and glypican, a further immunoprecipitation experiment is performed, in which both proteins are expressed in eukaryotic cells. Specifically, COS cells in 10 cm dishes are transfected with 2.5 µg of each of the glypican Xpress-tagged pcDNA3.1/His (Invitrogen) and sclerostin FLAG (Asp-Tyr-Lys-Asp-Asp-Asp-Asp-Lys)-tagged pFLAG-CMV-2 (Kodak) expression plasmids. At 36 h after transfection, cells are dissolved in 1 ml of lysis buffer [25 mM Tris/HCl (pH8.0)/150 mM NaCl/10% (v/v) glycerol/5 mM $MgCl_2$/2 mM EDTA/0.3°)/0 (v/v) Nonidet P40/5 mM NaF/0.5 mM PMSF/2 µg/ml aprotinin] and debris is discarded after centrifugation. Whole cell lysate is measured for protein quantity; 300 µg is used in the following steps: 1.5 µg (anti-Xpress; Invitrogen) or 1 µg (anti-FLAG M2; Sigma) of antibody is added to the lysates, which were then rotated at 4° C. for 1 h. Then 20 µl of Protein A-Sepharose beads (Amersham) is added and rotated for a further 2 h at 4° C. The beads are washed with lysis buffer three times and with PBS once. Proteins are eluted with SDS/PAGE sample buffer and boiled for 5 min. Western blotting is performed essentially as described in Maniatis et al. using an antibody against the Flag-tag or an antibody against native Sclerostin to show the presence of sclerostin in the immune complex, confirming that sclerostin binds to glypican.

6.2. $I^{125}$ Sclerostin Binding to Glypican.

In order to exclude a possible role of tags in the precipitation experiments, we perform a binding experiment with $I^{125}$-labeled sclerostin. COS cells are transfected with glypican containing a His-tag (see above). Sclerostin is radiolabeled with $I^{125}$ using the Chloramine-T method. The cells are subsequently affinity-labeled with radioactive sclerostin essentially as described by Yamashita et al. (Yamashita et al. 1995, Osteogenic protein-1 binds to activin type-II receptors and induces certain activin like effects. J. Cell Biol; 130:217-226). In brief, cells are incubated on ice for 3 hours with radioactive Sclerostin. After incubation, cells are washed and cross-linking is performed using 45 mM DSS (Disuccinimidyl suberate) and 3 mM BS (Bis(sulfo-succinimidyl) suberate) (Pierce) for 15 minutes. Cells are washed, scraped and lysed. Lysates are incubated with an anti-HIS antibody (Qiagen) and immune complexes are precipitated by adding ProteinA Sepharose (Amersham). Samples are washed, boiled in SDS sample buffer and subjected to SDS-PAGE. Gels are dried and scanned with STORM imaging system (Amersham), confirming that sclerostin binds to glypican.

6.3 ForteBio's Octet System Using Recombinant Glypicans and Sclerostin.

Sclerostin is expressed, purified and chemically coupled to biotin, after which the complex is further purified using two rounds of gel filtration to remove free biotin. Sclerostin-biotin is captured at concentrations between 20 and 25 µg/ml onto the surface of ForteBio's streptavidin sensors (Cat.#18-5003, ForteBio, Menlo Park, Calif.). Using standard kinetic assay formats developed by ForteBio, sensors containing immobilised Sclerostin are used to probe COS cell lysates where glypican is overexpressed. The kinetics of the interaction between sclerostin and glypigan are monitored in real-time using ForteBio's Octet QK System (Cat.#30-5005, ForteBio, Menlo Park, Calif.) as the complex forms.

Separate quantification of the native and his-tagged glypigan allows determination of the binding affinity (KD) of its interaction with Sclerostin. Confirmation that the complex is indeed formed between Sclerostin and glypigan and not another protein, is gained by using anti-histag antibody to generate a further signal as it complexes with his-tagged glypigan.

In the alternative an anti-glypigan antibody may be used that does not interfere with the formation of the Sclerostin-glypigan complex.

Instead of using expressed and purified Sclerostin, which is subsequently coupled to biotin and further purified, SOST may be modified such that it is expressed as a fusion protein with a biotin moiety.

These experiments can be repeated but using the BiaCore system in which the interaction with a purified form of the glypigan protein (native or his-tagged) would be used.

Example 7

Inhibition of Sclerostin—Glypican interaction

In order to confirm the interaction between sclerostin—glypican, we use anti-glypican antibodies and anti-sclerostin antibodies in a Western-blot assay. In short, GST-purified glypican and Xpress-tagged sclerostin as described in Example 6 is used, but now anti-glypican antibodies or anti-sclerostin antibodies are added. The results demonstrate that sclerostin no longer co-precipitates with Glypican. Thus, binding between sclerostin and glypican is abolished by either anti-glypican antibodies or anti-sclerostin antibodies.

ForteBio's Octet System using recombinant glypicans and sclerostin as described above under 6.3 is repeated in the presence or absence of anti-glypican antibodies and anti-sclerostin antibodies, confirming the abolishment of this specific interaction.

These experiments can be repeated with other molecules in order to identify specific inhibitors of this interaction.

Example 8

Inhibiting Glypican Enhances Bone Formation

In order to further confirm the role of the sclerostin—glypican interaction in bone formation, we use the progenitor mesenchymal cell line KS483, which has been shown to endogenously express glypican. Bone formation is monitored by the effects upon the BMP-induced alkaline phosphatase response, essentially as described by van Bezooijen et al. (2004). [JEM, Volume 199, Number 6, 805-814] Alkaline phosphatase is a marker for bone formation.

Short hairpin RNA constructs are made, intended to silence expression of the glypicans in these cells. The shRNA constructs are stably transfected into the KS483 cells. BMP-induced production of alkaline phosphatase, in the presence of sclerostin, is greater in those cells in which glypican(s) are being silenced.

Example 9

In Vivo Validation of the Sclerostin-Glypican Interaction 9.1 Sclerostin-Glypican Inhibits Bone Formation In Vivo To characterize the in vivo mechanism by which sclerostin-glypican inhibits bone formation, we use the assay described in Example 1, that is, a simple and rapid in vivo bioassay to determine sclerostin activity based on in vivo electroporation of naked DNA constructs into the mouse muscle (R. van Bezooijen et al., 2007 JBMR). Electroporation of BMP naked DNA strongly induces large amounts of bone in the muscle within two weeks. Co-injection of sclerostin naked DNA completely prevented this (see Example 1). We now use this assay to test the effects of different sclerostin (deletion) mutants on BMP-induced effects of subsequent bone formation, and interactions with other factors (including identified co-factors for sclerostin). As already shown in Example 1, when BMP was electroporated into the muscle, bone is formed. In contrast, electroporation of the controls, i.e. empty vector and vector expressing SOST, do not result in bone formation. Sclerostin co-electroporated with BMP on the other hand inhibits bone formation.

9.2 Mutated SOST does not Inhibit Bone Formation

Mutant forms of sclerostin are generated by PCR using the high fidelity thermostable DNA polymerase Pfu Ultra (Stratagene). Nucleotide sequences are verified by DNA sequencing. Expression of the mutants is validated by the TNT coupled rabbit reticulocyte lysate system (Promega) and subsequent verification by Western blot analysis using anti-sclerostin antibodies as described in Example 6.

Sclerostin having a mutation of the SLIT-domain is co-electroporated with BMP, and results in bone formation in normal muscle. Thus, mutated sclerostin cannot properly inhibit BMP induced bone formation.

9.3 Effect of Glypican on Bone Formation Inhibited by Sclerostin

The effect of glypican on bone formation induced by BMP-7 is further evaluated in cell culture. Specifically, dose response curves of bone formation for different concentrations of cDNA of sclerostin transfected together with a single BMP cDNA concentration are established, expressed as BMP-induced alkaline phosphatase response (see Example 8). Co-transfection with SOST-expression vectors reduces BMP-induced bone formation. The effect of sclerostin on BMP-induced bone formation is probably due to endogenous glypican.

At the 50% dose response level of SOST, glypican is added. Co-transfection of glypican further reduces bone formation so long as the glypican(s) are not at their maximum endogenous levels in the cell.

Similarly, when antisense agents, siRNA or ribozymes directed against glypican are introduced in the cell in addition to sclerostin and BMP-7 constructs, BMP-induced bone formation is increased. Substantially the same results are obtained when we introduce anti-sclerostin antibodies (see above), antisense agents, siRNA or ribozymes directed against sclerostin are introduced in the cell in addition to sclerostin and BMP-7 constructs, i.e. BMP-induced bone formation is increased.

Thus, the absence or reduction of glypican (s) reduces or abolishes the ability of sclerostin to inhibit BMP-induced bone formation, and an anti-glypican antibody or small molecule compound directed against glypican can abolish these effects of glypican (s).

9.4 siRNA Directed Against Glypicans Inhibits Sclerostin Activity In Vivo

In order to further evaluate the potential in vivo role of siRNA, the experiment described in Example 9.3 is repeated but now said siRNA is electroporated in mice muscles essentially as described in Kishida et al. (2004 J. Gene Med. 6: 105-110; Sequence-specific gene silencing in murine muscle induced by electroporation-mediated transfer of siRNA"). In short, siRNA duplexes corresponding to the regions identified in Example 9.3 are delivered by electroporation into the tibial muscle of BALB-mice. Expression constructs of BMP-7, sclerostin and/or glypican are also delivered. Bone formation in muscle is assayed by X-ray histology as described in Example 1. When siRNA directed against glypicans is co-delivered with glypican, sclerostin and BMP-7, or when co-delivered with sclerostin and BMP-7, bone formation is enhanced compared to controls in which only glypican, sclerostin and BMP-7, or sclerostin and BMP-7, are delivered, respectively. These results confirm the potential role of siRNA in in vivo treatment.

Materials and Methods to the Examples

Recombinant human BMP4, recombinant mouse Wnt3a (rmWnt3a), recombinant human sclerostin, recombinant mouse noggin, and recombinant human dkk1 were all purchased from R&D Systems Europe Ltd. (Abingdon, UK). The BMP-responsive luciferase reporter construct BRE-luc and the expression vectors for constitutive active BMP receptors mouse Activin receptor-like kinase 2 (caALK2) and mouse caALK6 were previously described (Korchynskyi, 2002). A modified Wnt-responsive luciferase reporter construct TBE-luc consisting of a minimal Wnt responsive promoter (4 repeats of TCF-4 binding element) driving expression of a Gal4VP16 fusion product combined with a responsive UAS-luciferase reporter was kindly provided by C. Breukel, Department of Human Genetics, Leiden University Medical Center, Leiden, The Netherlands. Expression constructs for mouse Wnt1, human/mouse hybrid Wnt3, and mouse Wnt3a were generously provided by Dr. R. Nusse, Stanford University Medical Center, California, USA.

Values are expressed as mean±SEM. Statistical differences between values were examined by one-way ANOVA followed by Bonferroni's Multiple Comparison Test and considered to be significant different at $p<0.05$.

Cell cultures—Mouse mesenchymal KS483 were cultured in alpha-MEM and mouse mesenchymal C3H10T1/2 cells and rat and human osteosarcoma cells, UMR106 and U2OS, respectively, in DMEM (GIBCO BRL, Breda, The Netherlands) supplemented with penicillin/streptomycin (Invitrogen, Breda, The Netherlands) and 10% fetal calf serum (FCS) (Integro B. V., Zaandam, The Netherlands).

Transfections and reporter assays—KS483, C3H10T1/2, or U2OS cells were seeded at a density of 10 000, 20 000, and 20 000 cells/well in 24-wells plates, respectively, and transiently transfected with either BRE-luc or TBE-luc using Fugene™ 6 transfection reagent according to the manufacture's protocol (Roche, Basel, Switzerland). Wnt1, Wnt3, and Wnt3a expression vectors were co-transfected when needed. To correct for transfection efficiency, *Renilla luciferase* vector was co-transfected (pRL-SV40; Promega, Leiden, The Netherlands). 12 Hours after transfection, medium was changed for medium containing 0.2% FCS and cells were treated as described in the results section. Luciferase assays were performed with the Dual-Luciferase Reporter assay system according to the manufacturer's instructions (Promega, Leiden, The Netherlands). Firefly luciferase activity was corrected for *Renilla luciferase* activity to control for differences in transfection efficiency. Values are expressed as mean± SEM. Statistical differences between values were examined by one-way ANOVA followed by Bonferroni's Multiple Comparison Test and considered to be significant different at $p<0.05$.

What is claimed is:

1. An in vitro method for identifying an inhibitor of the glypican-sclerostin interaction comprising the steps of:

a) contacting sclerostin with glypican in the presence and absence of the candidate inhibitor under conditions permitting the binding of the glypican to sclerostin; and b1) measuring binding of the glypican to sclerostin, wherein a decrease in binding in the presence of the candidate inhibitor, relative to binding in the absence of the candidate inhibitor, identifies the candidate inhibitor as an inhibitor of the glypican-sclerostin interaction, or b2) measuring the signaling response induced by the glypican-sclerostin interaction in the presence of the candidate inhibitor, and comparing it with the signaling response induced by the glypican-sclerostin interaction in the absence of the candidate inhibitor, wherein a change in the signaling response identifies the candidate inhibitor as an inhibitor of the glypican-sclerostin interaction;

wherein the glypican is selected from the group consisting of glypican-1, glypican-2, glypican-3, glypican-4, glypican-5, and glypican-6.

2. The method according to claim 1, wherein said measuring in step b1) is performed using a method selected from the group consisting of label displacement, surface plasmon resonance, fluorescence resonance energy transfer, bioluminescence resonance energy transfer, fluorescence quenching, and fluorescence polarization.

3. The method according to claim 1, wherein in step b2) a change in the signaling response by at least 10% in the presence of the candidate inhibitor relative to the absence of the candidate inhibitor identifies the candidate inhibitor as an inhibitor of the glypican-sclerostin interaction.

* * * * *

UNITED STATES PATENT AND TRADEMARK OFFICE
CERTIFICATE OF CORRECTION

| | | |
|---|---|---|
| PATENT NO. | : 8,541,177 B2 | Page 1 of 1 |
| APPLICATION NO. | : 12/160761 | |
| DATED | : September 24, 2013 | |
| INVENTOR(S) | : Chan | |

It is certified that error appears in the above-identified patent and that said Letters Patent is hereby corrected as shown below:

In the Specification

In column 3 at line 57, Change "mass" to --mass.--.

In column 4 at line 31, Change "Calm," to --Calos,--.

In column 4 at line 49, Change "of"" to --of'--.

In column 6 at line 12, Change "an," to --an--.

In column 6 at line 49, Change "at al." to --et al.--.

In column 8 at line 10, Change "ing."" to --ing..."--.

In column 9 at line 51, Change "30%240%," to --30%, 40%,--.

In column 13 at lines 52-53, Change "scleroteosis" to --sclerosteosis--.

In column 13 at line 55, Change "scleroteosis" to --sclerosteosis--.

In column 14 at line 52, Change "antibody," to --antibody--.

In column 17 at line 48, Change "08N158)," to --Q8N158),--.

In column 17 at line 60, Change "at al.," to --et al.,--.

In column 17 at line 63, Change "at al.," to --et al.,--.

In column 28 at line 23, Change "1d" to --Id--.

In column 28 at line 49, Change "(PGDF)." to --(PDGF).--.

In column 31 at line 43, Change "is" to --it--.

In column 32 at line 51, Change "fl-galactosidase" to --β-galactosidase--.

In column 33 at line 5, Change "alin-TPBS;" to --albumin-TPBS;--.

In column 33 at line 20, Change "EDTA/0.3°)/0" to --EDTA/0.3%--.

Signed and Sealed this
Third Day of June, 2014

Michelle K. Lee
*Deputy Director of the United States Patent and Trademark Office*